United States Patent
Bagwell et al.

(10) Patent No.: US 9,987,468 B2
(45) Date of Patent: Jun. 5, 2018

(54) REDUCED FORCE DEVICE FOR INTRAVASCULAR ACCESS AND GUIDEWIRE PLACEMENT

(71) Applicant: Actuated Medical, Inc., Bellefonte, PA (US)

(72) Inventors: Roger B Bagwell, Bellefonte, PA (US); Ryan S Clement, State College, PA (US); Maureen L Mulvihill, Bellefonte, PA (US); Casey A Scruggs, Middleburg, PA (US); Kevin A Snook, State College, PA (US)

(73) Assignee: Actuated Medical, Inc., Bellefonte, PA (US)

( * ) Notice: Subject to any disclaimer, the term of this patent is extended or adjusted under 35 U.S.C. 154(b) by 0 days. days.

(21) Appl. No.: 15/205,357

(22) Filed: Jul. 8, 2016

(65) Prior Publication Data

US 2016/0346519 A1    Dec. 1, 2016

Related U.S. Application Data

(60) Provisional application No. 62/189,956, filed on Jul. 8, 2015.

(51) Int. Cl.
*A61M 25/09* (2006.01)
*A61B 5/15* (2006.01)
(Continued)

(52) U.S. Cl.
CPC ... *A61M 25/09041* (2013.01); *A61B 5/15003* (2013.01); *A61B 5/150137* (2013.01);
(Continued)

(58) Field of Classification Search
CPC ............................................. A61M 25/09041
(Continued)

(56) References Cited

U.S. PATENT DOCUMENTS

| 4,428,748 A | 1/1984 | Peyman |
| 4,553,541 A | 11/1985 | Burns |

(Continued)

FOREIGN PATENT DOCUMENTS

| EP | 0266058 | 5/1988 |
| EP | 1647255 | 4/2006 |

(Continued)

OTHER PUBLICATIONS

United States Patent and Trademark Office; Office Action; Office Action from U.S. Appl. No. 14/522,681; pp. 1-60; publisher United States Patent and Trademark Office; published Alexandria, Virginia, USA; copyright and dated Mar. 30, 2017; (60 pages).

(Continued)

*Primary Examiner* — Michael C Stout
(74) *Attorney, Agent, or Firm* — Metz Lewis Brodman Must O'Keefe LLC

(57) ABSTRACT

A device for penetrating tissue with reduced force and placing a guidewire is provided. The device includes a driving actuator generating reciprocating motion. A penetrating member having a lumen dimensioned to accommodate a guidewire is provided. A coupler mechanically connects the driving actuator and the penetrating member to transfer the reciprocating motion to the penetrating member. The penetrating member may be coaxial or axially offset from the driving actuator. At least one frictional member facilitates the movement of the guidewire through the lumen for placement at the target tissue. The frictional member(s) may be operated manually or by a guidewire actuator. A housing may also be provided including a channel also dimensioned to accommodate the guidewire, and may further include the frictional member(s) for facilitating movement of the guidewire. The channel and lumen are aligned to permit placement of the guidewire at the target site.

32 Claims, 27 Drawing Sheets

(51) Int. Cl.
  *A61B 10/02*     (2006.01)
  *A61M 25/06*    (2006.01)
  *A61B 17/34*     (2006.01)
  *A61M 5/32*      (2006.01)
  *A61M 25/00*    (2006.01)
  *A61B 17/32*     (2006.01)
  *A61B 17/00*     (2006.01)
  *A61B 90/00*     (2016.01)

(52) U.S. Cl.
  CPC ...... *A61B 5/150389* (2013.01); *A61B 10/025* (2013.01); *A61B 10/0233* (2013.01); *A61B 17/3401* (2013.01); *A61B 17/3415* (2013.01); *A61B 17/3476* (2013.01); *A61M 5/3287* (2013.01); *A61M 25/0084* (2013.01); *A61M 25/06* (2013.01); *A61B 17/320068* (2013.01); *A61B 2010/0208* (2013.01); *A61B 2017/00115* (2013.01); *A61B 2017/00123* (2013.01); *A61B 2090/064* (2016.02); *A61M 2025/09116* (2013.01)

(58) Field of Classification Search
  USPC .................................................. 600/566, 565
  See application file for complete search history.

(56) References Cited

U.S. PATENT DOCUMENTS

| | | | |
|---|---|---|---|
| 4,623,335 A | 11/1986 | Jackson | |
| 4,648,406 A | 3/1987 | Miller | |
| 4,771,660 A | 9/1988 | Yacowitz | |
| 4,801,293 A | 1/1989 | Jackson | |
| 4,911,161 A | 3/1990 | Schechter | |
| 5,024,662 A | 6/1991 | Menes et al. | |
| 5,151,083 A | 9/1992 | Pichler | |
| 5,217,478 A | 6/1993 | Rexroth | |
| 5,221,282 A | 6/1993 | Wuchinich | |
| 5,320,613 A * | 6/1994 | Houge ................. | A61M 25/00 604/256 |
| 5,403,276 A | 4/1995 | Schechter | |
| 5,449,370 A | 9/1995 | Vaitekunas | |
| 5,471,102 A | 11/1995 | Becker et al. | |
| 5,526,820 A | 6/1996 | Khoury | |
| 5,575,789 A | 11/1996 | Bell | |
| 5,647,851 A | 7/1997 | Pokras | |
| 5,681,283 A | 10/1997 | Brownfield | |
| 5,711,302 A | 1/1998 | Lampropoulos | |
| 5,728,089 A | 3/1998 | Lal et al. | |
| 5,728,130 A | 3/1998 | Ishikawa et al. | |
| 5,729,077 A | 3/1998 | Newnham et al. | |
| 5,735,813 A | 4/1998 | Lewis | |
| 5,769,086 A * | 6/1998 | Ritchart ............. | A61B 10/0275 600/566 |
| 5,840,026 A | 11/1998 | Uber, III et al. | |
| 5,843,109 A | 12/1998 | Mehta | |
| 5,865,764 A | 2/1999 | Moorhead | |
| 5,871,470 A | 2/1999 | McWha | |
| 5,885,226 A | 3/1999 | Rubinstein et al. | |
| 5,954,701 A | 9/1999 | Matalon | |
| 6,019,775 A | 2/2000 | Sakurai | |
| 6,019,776 A | 2/2000 | Preissman et al. | |
| 6,068,604 A | 5/2000 | Krause | |
| 6,096,004 A | 8/2000 | Meglan et al. | |
| 6,190,333 B1 * | 2/2001 | Valencia .......... | A61M 25/09041 600/585 |
| 6,245,028 B1 | 6/2001 | Furst et al. | |
| 6,273,861 B1 | 8/2001 | Bates et al. | |
| 6,379,371 B1 | 4/2002 | Novak et al. | |
| 6,402,701 B1 | 6/2002 | Kaplan | |
| 6,423,014 B1 | 7/2002 | Churchill et al. | |
| 6,443,910 B1 | 9/2002 | Krueger et al. | |
| 6,465,936 B1 | 10/2002 | Knowles et al. | |
| 6,402,769 B1 | 11/2002 | Boukhny | |
| 6,491,708 B2 | 12/2002 | Madan et al. | |
| 6,497,714 B1 | 12/2002 | Ishikawa et al. | |
| 6,514,267 B2 | 2/2003 | Jewett | |
| 6,602,229 B2 | 8/2003 | Coss | |
| 6,623,429 B2 | 9/2003 | Percival | |
| 6,629,922 B1 | 10/2003 | Puria | |
| 6,664,712 B2 | 12/2003 | Rayner | |
| 6,673,086 B1 | 1/2004 | Hofmeier et al. | |
| 6,689,087 B2 | 2/2004 | Pal et al. | |
| 6,702,761 B1 | 3/2004 | Damadian | |
| 6,718,196 B1 | 4/2004 | Mah et al. | |
| 6,726,698 B2 | 4/2004 | Cimino | |
| 6,730,043 B2 | 5/2004 | Krueger et al. | |
| 6,785,572 B2 | 8/2004 | Yanof et al. | |
| 6,817,973 B2 | 11/2004 | Merril et al. | |
| 6,869,439 B2 | 3/2005 | White et al. | |
| 6,939,317 B2 | 9/2005 | Zacharias | |
| 6,942,677 B2 | 9/2005 | Nita et al. | |
| 6,984,220 B2 | 1/2006 | Wuchinich | |
| 7,018,343 B2 | 3/2006 | Plishka | |
| 7,025,774 B2 | 4/2006 | Freeman et al. | |
| 7,206,626 B2 | 4/2007 | Quaid, III | |
| 7,297,131 B2 | 11/2007 | Nita | |
| 7,335,997 B2 | 2/2008 | Wiener | |
| 7,364,567 B2 | 4/2008 | Beyerlein | |
| 7,374,544 B2 | 5/2008 | Freeman et al. | |
| 7,518,479 B2 | 4/2009 | Mask et al. | |
| 7,585,280 B2 | 9/2009 | Wilson | |
| 7,618,409 B2 | 11/2009 | Hochman | |
| 7,648,468 B2 | 1/2010 | Boecker et al. | |
| 7,651,475 B2 | 1/2010 | Angel et al. | |
| 7,651,490 B2 | 1/2010 | Boukhny et al. | |
| 7,654,825 B2 | 2/2010 | Ray | |
| 7,776,027 B2 | 8/2010 | Manna et al. | |
| 7,896,833 B2 | 3/2011 | Hochman | |
| 7,922,689 B2 | 4/2011 | Lechner | |
| 7,955,301 B1 | 6/2011 | McKay | |
| 8,043,229 B2 | 10/2011 | Mulvihill et al. | |
| 8,043,308 B2 | 10/2011 | Bittenson | |
| 8,075,496 B2 | 12/2011 | Deck | |
| 8,142,365 B2 | 3/2012 | Miller | |
| 8,177,753 B2 | 5/2012 | Vitullo et al. | |
| 8,231,645 B2 | 7/2012 | List | |
| 8,308,721 B2 | 11/2012 | Shibata et al. | |
| 8,328,738 B2 | 12/2012 | Frankhouser et al. | |
| 2001/0014785 A1 | 8/2001 | Sussman et al. | |
| 2002/0010390 A1 | 1/2002 | Guice | |
| 2002/0026127 A1 | 2/2002 | Balbierz et al. | |
| 2002/0042594 A1 * | 4/2002 | Lum ................... | A61B 5/053 604/117 |
| 2002/0049462 A1 | 4/2002 | Friedman | |
| 2002/0077589 A1 | 6/2002 | Tessari | |
| 2002/0109433 A1 | 8/2002 | Rayner | |
| 2002/0183774 A1 | 12/2002 | Witt et al. | |
| 2002/0198555 A1 | 12/2002 | White et al. | |
| 2003/0040737 A1 | 2/2003 | Merril | |
| 2003/0078495 A1 | 4/2003 | Goodwin | |
| 2003/0109871 A1 | 6/2003 | Johnson et al. | |
| 2003/0195468 A1 | 10/2003 | Lal et al. | |
| 2003/0199899 A1 | 10/2003 | Boecker et al. | |
| 2003/0199909 A1 | 10/2003 | Boecker | |
| 2004/0010204 A1 | 1/2004 | Weber | |
| 2004/0010251 A1 | 1/2004 | Pitaru | |
| 2004/0024358 A1 | 2/2004 | Meythaler | |
| 2004/0049216 A1 | 3/2004 | Verdaasdonk | |
| 2004/0082884 A1 | 4/2004 | Pal | |
| 2004/0106894 A1 | 6/2004 | Hunter et al. | |
| 2004/0215080 A1 | 10/2004 | Lechner | |
| 2004/0260240 A1 | 12/2004 | Beyerlein | |
| 2005/0070458 A1 | 3/2005 | John | |
| 2005/0131345 A1 | 6/2005 | Miller | |
| 2005/0148940 A1 | 7/2005 | Miller | |
| 2005/0177201 A1 | 8/2005 | Freeman | |
| 2006/0058783 A1 | 3/2006 | Buchman, III | |
| 2006/0122555 A1 | 6/2006 | Hochman | |
| 2006/0129091 A1 * | 6/2006 | Bonnette ............ | A61B 17/22 604/93.01 |
| 2006/0135882 A1 | 6/2006 | Bleich | |
| 2006/0142657 A1 | 6/2006 | Quaid et al. | |

(56) References Cited

U.S. PATENT DOCUMENTS

| | | |
|---|---|---|
| 2006/0149141 A1 | 7/2006 | Sheets |
| 2006/0149161 A1 | 7/2006 | Wilson |
| 2006/0195043 A1 | 8/2006 | Rutherford |
| 2006/0224144 A1 | 10/2006 | Lee |
| 2007/0038129 A1 | 2/2007 | Kishimoto |
| 2007/0063618 A1 | 3/2007 | Bromfield |
| 2007/0079455 A1 | 4/2007 | Brewer |
| 2007/0088297 A1 | 4/2007 | Redding |
| 2007/0088376 A1 | 4/2007 | Zacharias |
| 2007/0106158 A1 | 5/2007 | Madan |
| 2007/0123888 A1 | 5/2007 | Bleich |
| 2007/0129628 A1 | 6/2007 | Hirsh |
| 2007/0129732 A1 | 6/2007 | Zacharias |
| 2007/0142766 A1 | 6/2007 | Sundar et al. |
| 2007/0191758 A1 | 8/2007 | Hunter et al. |
| 2007/0219496 A1 | 9/2007 | Kamen et al. |
| 2007/0250113 A1 | 10/2007 | Hegeman et al. |
| 2007/0255220 A1 | 11/2007 | King |
| 2008/0009791 A1 | 1/2008 | Cohen et al. |
| 2008/0021490 A1 | 1/2008 | Briggs et al. |
| 2008/0055028 A1* | 3/2008 | Mask ............... A61M 37/0084 335/229 |
| 2008/0097287 A1 | 4/2008 | Nelson |
| 2008/0103413 A1 | 5/2008 | Cicenas et al. |
| 2008/0139961 A1 | 6/2008 | Slama et al. |
| 2008/0147094 A1 | 6/2008 | Bittenson |
| 2008/0154188 A1 | 6/2008 | Hochman |
| 2008/0228104 A1 | 9/2008 | Uber et al. |
| 2008/0255444 A1 | 10/2008 | Li |
| 2009/0005703 A1 | 1/2009 | Fasciano |
| 2009/0069712 A1 | 3/2009 | Mulvihill et al. |
| 2009/0131830 A1 | 5/2009 | Freeman |
| 2009/0131832 A1 | 5/2009 | Sacristan Rock |
| 2009/0157044 A1 | 6/2009 | Liyanagama |
| 2009/0204119 A1 | 8/2009 | Bleich |
| 2009/0240205 A1 | 9/2009 | Wen |
| 2009/0247865 A1 | 10/2009 | Spohn et al. |
| 2009/0270759 A1 | 10/2009 | Wilson |
| 2010/0004558 A1* | 1/2010 | Frankhouser ........ A61B 10/025 600/567 |
| 2010/0010505 A1 | 1/2010 | Herlihy et al. |
| 2010/0036245 A1 | 2/2010 | Yu et al. |
| 2010/0036256 A1* | 2/2010 | Boukhny ............ A61F 9/00745 600/459 |
| 2010/0069828 A1* | 3/2010 | Steen ................. A61F 9/00745 604/22 |
| 2010/0069851 A1 | 3/2010 | Vad |
| 2010/0094143 A1 | 4/2010 | Mahapatra |
| 2010/0094310 A1 | 4/2010 | Waring et al. |
| 2011/0004159 A1 | 1/2011 | Nelson |
| 2011/0125107 A1 | 5/2011 | Slocum |
| 2011/0130758 A9 | 6/2011 | Bleich |
| 2011/0224623 A1 | 9/2011 | Velez Rivera |
| 2011/0298628 A1 | 12/2011 | Vad |
| 2012/0078231 A1* | 3/2012 | Hoshinouchi ... A61M 25/09041 604/528 |
| 2012/0210569 A1* | 8/2012 | Schmitt ........... A61M 25/09041 29/700 |
| 2012/0220942 A1* | 8/2012 | Hall ................. A61M 25/0606 604/164.1 |
| 2012/0232488 A1 | 9/2012 | Aviles |
| 2013/0072856 A1 | 3/2013 | Frankhouser et al. |
| 2014/0142553 A1 | 5/2014 | Poncon |
| 2014/0299568 A1 | 10/2014 | Browne |
| 2015/0182232 A1* | 7/2015 | Peterson ............ A61B 17/1624 606/80 |
| 2015/0297404 A1 | 10/2015 | Kang |
| 2015/0297449 A1 | 10/2015 | Browne |
| 2015/0306358 A1* | 10/2015 | Duffy .................... A61F 2/966 623/1.11 |

FOREIGN PATENT DOCUMENTS

| | | |
|---|---|---|
| JP | 9239031 | 9/1997 |
| JP | 2001346874 | 12/2001 |
| WO | 2004091693 | 10/2004 |
| WO | 2008086560 | 7/2008 |
| WO | 2008097609 | 8/2008 |
| WO | 2009083600 | 7/2009 |
| WO | 2009092164 | 7/2009 |
| WO | 2009097621 | 8/2009 |

OTHER PUBLICATIONS

Meyer, Jr., R.J., et al., Displacement Amplification of Electroactive Materials Using the Cymbal Flextensional Transducer, Sensors and Actuators A 87 (2001) 157-162.

Podder, T.K., et al., Effects of Velocity Modulation During Surgical Needle Insertion, Proceedings of the 2005 IEEE, Engineering in Medicine and Biology 27th Annual Conference, Sep. 1-4, 2005.

Luis, J., et al., Rectangular Cymbal Arrays for Improved Ultrasonic Transdermal Insulin Delivery, J. Acoust. Soc. Am., vol. 122, Issue 4, Oct. 2007.

Yang, M., et al., "Microneedle Insertion Force Reduction Using Vibratory Actuation", Biomedical Microdevices 6:3, 177-182, 2004.

Zorcolo, et al., Catheter Insertion Simulation With Combined Visual and Haptic Feedback, Center for Advanced Studies, Research and Development in Sardinia 09101 Uta (CA) Italy.

Piccin, et al., "A Robotized Needle Insertion Device for Percutaneous Procedures", Proceedings of IDETC/CIE 2005, 2006 ASME International Design Engineering Technical Conferences and Computers and Information in Engineering Conference, Long Beach, CA, USA, Sep. 24-28, 2005.

Loeffel, et al., Development of an Advanced Injection Device for Highly Viscous Materials, European Cells and Materials, vol. 11, Supp. 1, 2006, p. 51.

Dario, et al., Smart Surgical Tools and Augmenting Devices, IEEE Transactions on Robotics and Automation, vol. 19, No. 5, Oct. 2003, pp. 782-792.

Sonic Drill Could Go Into Space, R&D, Sep. 2000, p. 135.

Goethals, P., Tactile Feedback for Robot Assisted Minimally Invasive Surgery: An Overview, Division PMA, Department of Engineering, K.U. Leuven, Jul. 14, 2008.

Zorcolo, et al., "Catheter Insertion Simulation with Combined Visual and Haptic Feedback", Center for Advanced Studies, Research and Development in Sardinia, 09101 Uta (CA) Italy; Proceedings of The First PHANToM Users Research Symposium, May 21-22, 1999, Deutsches Krebsfordschungszentrum, Heidelberg, Germany.

Mark V ProVis Angiographic Injection System, Medrad, Inc., Copyright 2006-2010.

Kwon, et al., Realistic Force Reflection in the Spine Biopsy Simulator, IEEE International Conference on Robotics and Automation, 2001. Proceedings 2001 ICRA, May 21-26, 2001, Seoul, Korea 2001, vol. 2, 1358-1363.

R&D 100 Awards Winners Reveal 21st Century Technologies, 38th Annual R&D Awards, R&D Research & Development, Sep. 2000, p. 135.

Silicon-Based Ultrasonic Surgical Actuators, Amit Lal, Member, IEEE; Proceedings of the 20th Annual International Conference of the IEEE Engineering in Medicine and Biology Society, vol. 20, No. 6, 1998, pp. 2785-2790.

Terrett, et al., 3538 Study Assessing the Effectiveness of a Vibrating Dental Syringe Attachment, Pain Management, Oral Pathology, Malodor, and Indices, Mar. 13, 2004.

Hing, et al., Reality-Based Needle Insertion Simulation for Haptic Feedback in Prostate Brachytherapy, Proceedings of the 2006 IEEE International Conference on Robotics and Automation, Orlando, Florida, May 2006.

Hing, et al., Reality-Based Estimation of Needle and Soft-Tissue Interaction for Accurate Haptic Feedback in Prostate Brachytherapy Simulation, Program for Robotics, Intelligent Sensing, and

(56) References Cited

OTHER PUBLICATIONS

Mechatronics (PRISM) Labaoratory, Drexel University, Philadelphia, PA, Drexel University College of Medicine, Philadelphia, PA.
International Preliminary Report on Patentability for PCT Application No. PCT/AU2008/000019, dated Jul. 21, 2009.
International Search Report for PCT Application No. PCT/US2009/060387, dated May 18, 2010.
International Search Report for PCT Application No. PCT/US2009/056864, dated Apr. 26, 2010.
United States Patent and Trademark Office; Office Action; Office Action from U.S. Appl. No. 13/222,363;copyright and dated Dec. 11, 2014; pp. 1-9; publisher United States Patent and Trademark Office; Published Alexandria, Virginia, USA; copyright and dated Dec. 11, 2014; (9 pages).
United States Patent and Trademark Office; Office Action; Office Action from U.S. Appl. No. 14/329,177; copyright and dated Nov. 18, 2014; pp. 1-19; publisher United States Patent and Trademark Office; Published Alexandria, Virginia, USA; copyright and dated Nov. 18, 2014; (19 pages).
International Searching Authority; International Search Report and Written Opinion of the International Searching Authority;International Application No. PCT/US2014/062099; Patent Cooperation Treaty; pp. 1-10; publisher United States International Searching Authority; Published Alexandria Virginia, US; copyright and dated Mar. 11, 2015; (10 pages).
Shin-El T, et al., Reduction of Insertion Force of Medical Devices Into Biological Tissues by Vibration, Japanese Journal of Medical Electronics and Biological Engineering, (2001) 39:292-6.
Marx, J.A., et al., The Effect of Vibration on the Needle Dynamics of Sclerotherapy, Australian College of Phlebology, 12th Annual Scientific Meeting, 2008; Gold Coast, Australia.
Huang, Y., et al., A Piezoelectric Vibration-Based Syringe for Reducing Insertion Force, IOP Conference Series: Materials Science and Engineering, 2012, 42:012020.
Khalaji, I., et al., Analysis of Needle-Tissue Friction During Vibration-Assisted Needle Insertion, Intelligent Robots and Systems (IROS), 2013 IEEE/RSJ International Conference on; 2013 Nov. 7-10, 2013, pp. 4099-4104.
Begg, ND, et al., Audible Frequency Vibration of Puncture-Access Medical Devices. Medical Eng Phys 2014; 36:371-7.
Ramasubramanian, MK, et al., Mechanics of a Mosquito Bite With Applications to Microneedle Design. Raleigh, NC 27695-7810, USA, North Carolina State University, 2008.
Mahvash, M., et al., Fast Needle Insertion to Minimize Tissue Deformation and Damage. IEEE International Conference on Robotics and Automation 2009: 3097-102.
Mahvash, M., et al, Mechanics of Dynamic Needle Insertion into a Biological Material. IEEE Trans Biomed Eng 2009.
Van Gerwen, D.J., et al., Needle-Tissue Interaction Forces—A Survey of Experimental Data. Med Eng Phys 2012; 34:665-80.
Yang, M., et al., Microneedle Insertion Force Reduction Using Vibrator Actuation. Biomed Microdevices, 2004, 6:177-182, Kluwer Academic Publishers, The Netherlands.
Cohen, D., This Won't Hurt a Bit. New Scientist, 2002:21.
Kong, XQ, et al., Mosquito Proboscis: An Elegant Biomicroelectromechanical System. Phys Rev E Stat Nonlin Soft Matter Phys 2010, 82:011910.
Chan, K.K., et al., The Mode of Action of Surgical Tissue Removing Devices, IEEE 1985 Ultrasonics Symposium, 1985 Oct. 16-18, 1985, p. 855-9.
Muralidharan, K., Mechanics of Soft Tissue Penetration by a Vibrating Needle, Baltimore, Maryland, University of Maryland Baltimore County, 2007.
International Searching Authority; International Search Report and Written Opinion of the International Searching Authority; International Application No. PCT/US16/41499; Patent Cooperation Treaty; pp. 1-8; publisher United States International Searching Authority; Published Alexandria, Virginia, US; copyright and dated Oct. 20, 2016; (8 pages).
Castelvecchi, D., This Bite Won't Hurt a Bit—Science News. Science News 2008:11.
United States Patent and Trademark Office; Office Action; Office Action from U.S. Appl. No. 14/522,681; pp. 1-36; publisher United States Patent and Trademark Office; published Alexandria, Virginia, USA; copyright and dated Aug. 29, 2017; (36 pages).
United States Patent and Trademark Office; Office Action; Office Action from U.S. Appl. No. 14/522,681; pp. 1-15; publisher United States Patent and Trademark Office; published Alexandria, Virginia, USA; copyright and dated Apr. 3, 2018; copy enclosed (15 pages).

\* cited by examiner

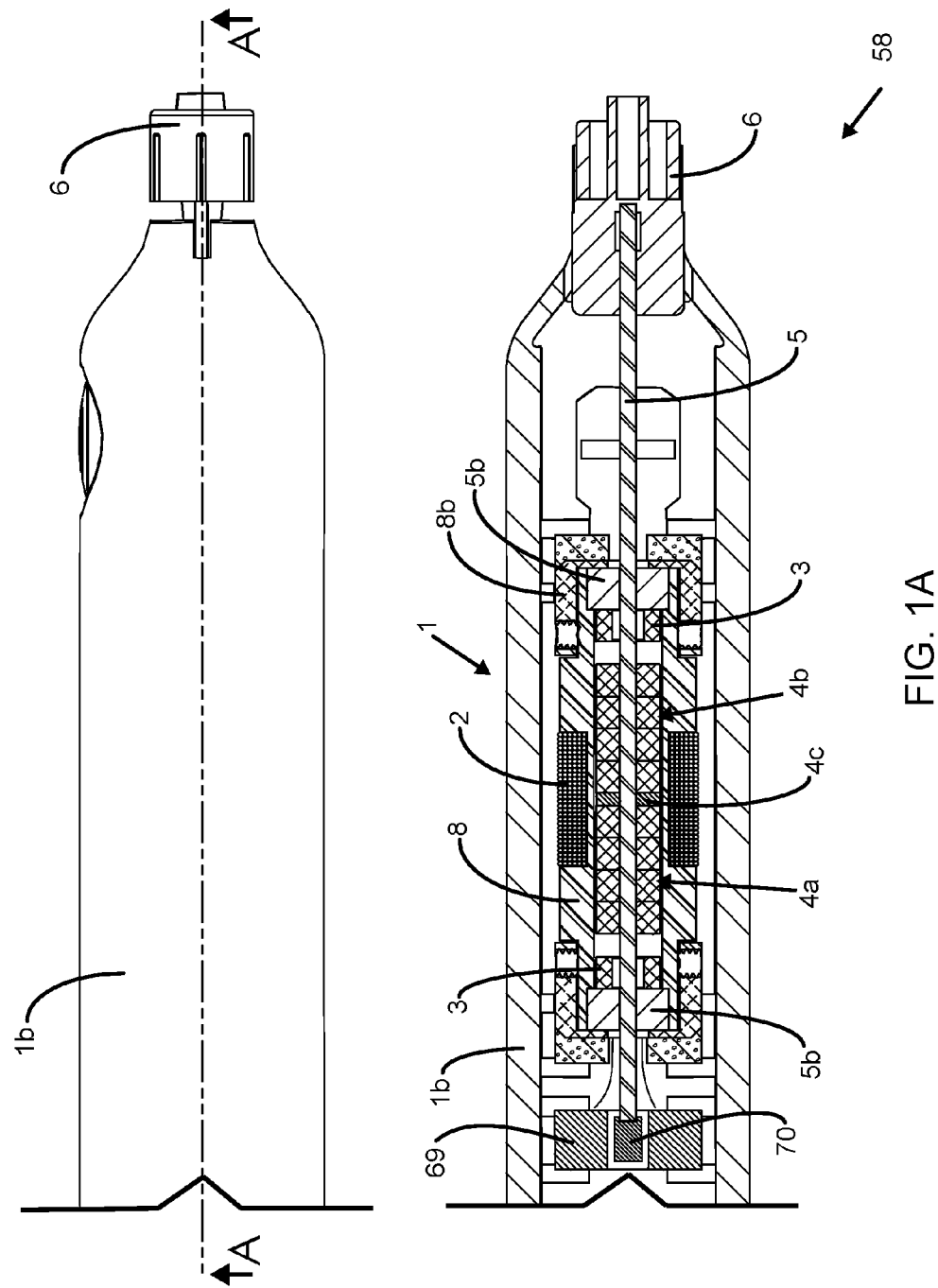

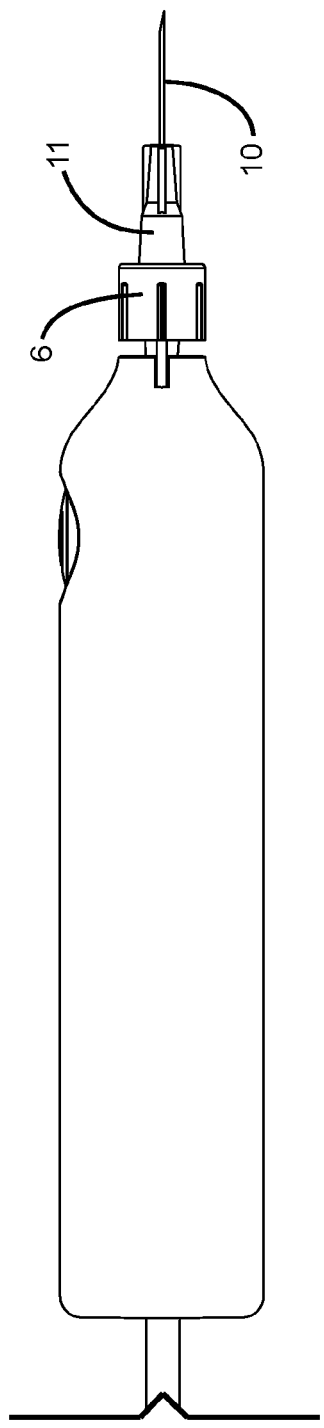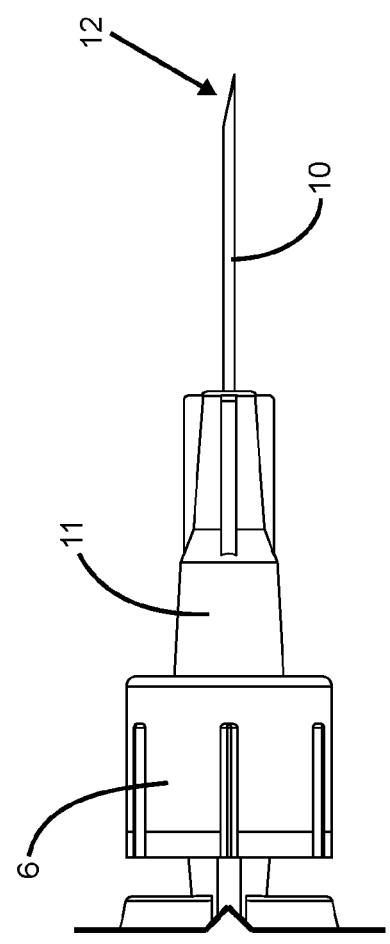
FIG. 2A
FIG. 2B

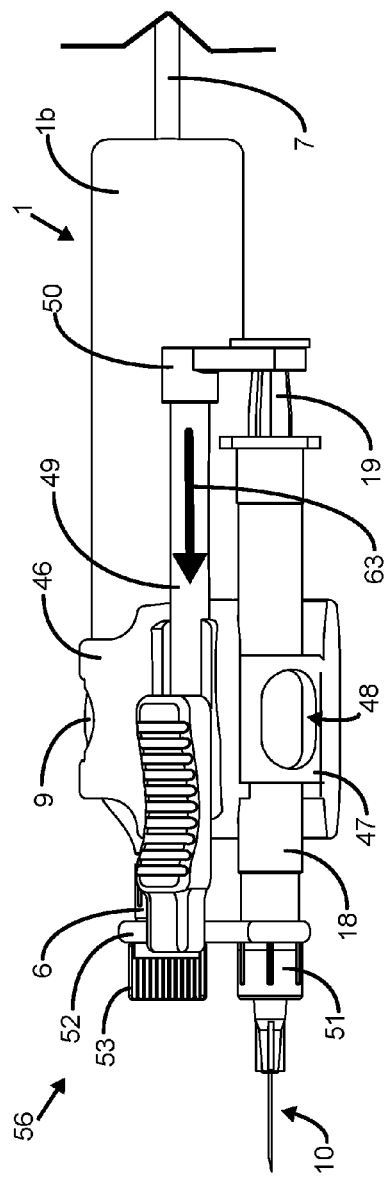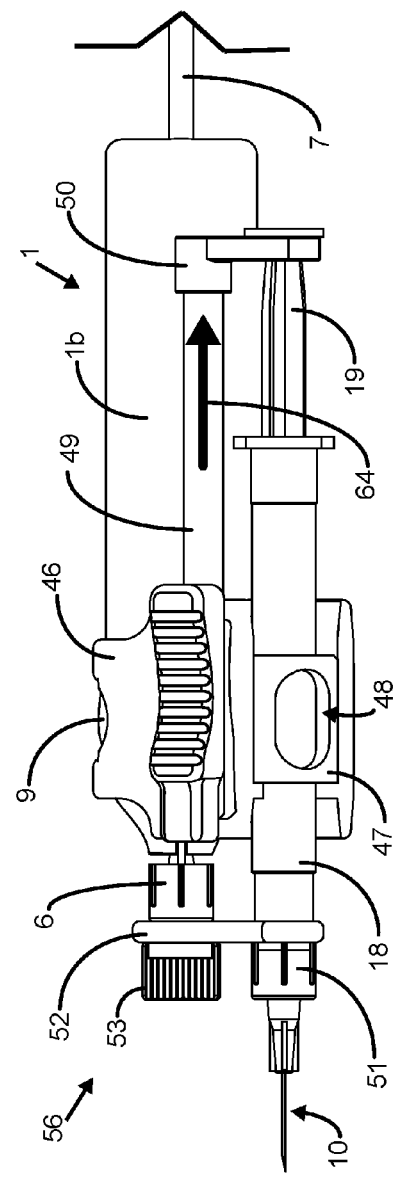

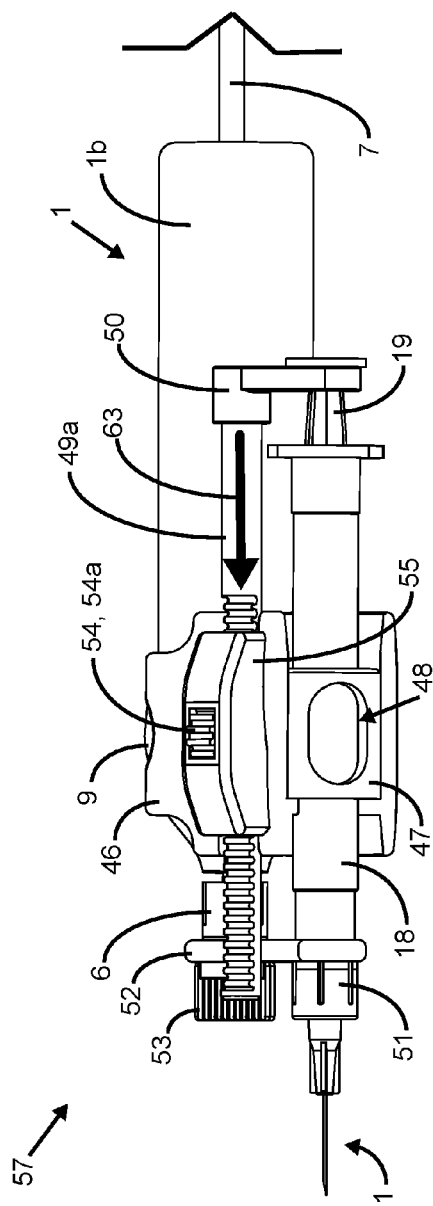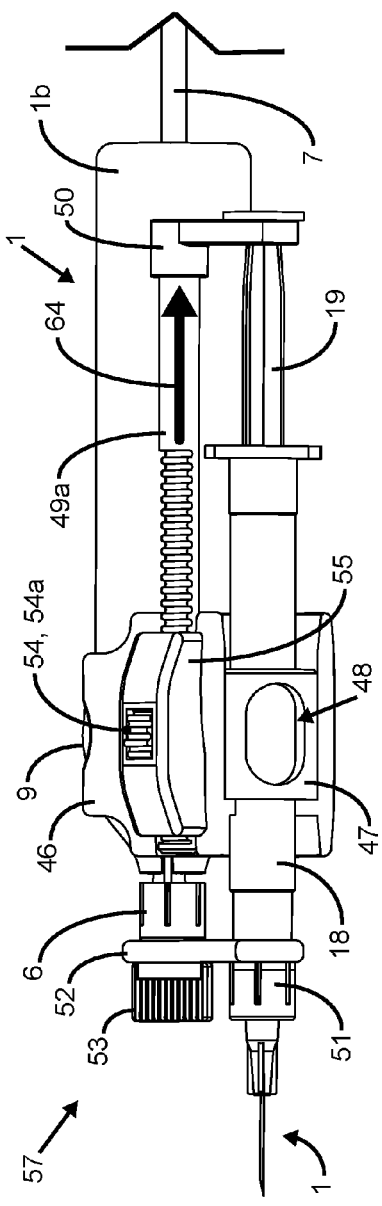

REDUCED FORCE DEVICE FOR INTRAVASCULAR ACCESS AND GUIDEWIRE PLACEMENT

CROSS REFERENCE TO RELATED APPLICATIONS

The present application claims the benefit of currently pending U.S. Provisional Application Ser. No. 62/189,956, filed Jul. 8, 2015, the contents of which are incorporated by reference herein in its entirety.

STATEMENT REGARDING FEDERALLY SPONSORED RESEARCH OR DEVELOPMENT

This invention was made with government support under RR024943 awarded by the National Institutes of Health. The government has certain rights in the invention.

FIELD OF THE INVENTION

The present invention generally pertains to handheld medical, veterinary, and pre-clinical or laboratory research devices, and more specifically to electrically-powered, handheld devices that utilize oscillatory actuation to aid penetration through various tissues within a body for the delivery or removal of bodily fluids, tissues, nutrients, medicines, therapies, or for obtaining percutaneous access to body compartments (e.g. vasculature, spinal cavity) for secondary placement of medical devices (e.g. guidewires, catheters).

BACKGROUND

In the fields of medicine, veterinary, and pre-clinical or laboratory research, the need to insert penetrating members (such as needles, lancets and catheters) into living tissues is ubiquitous. Some of the reasons necessitating tissue penetration and insertion of penetrating members include: to inject medications and vaccines, to obtain samples of bodily fluids such as blood, to acquire a tissue sample such as for biopsy, or to provide short or long term access to the vascular system such as intravenous (IV) catheter and/or guidewire placement.

Of the 39 million patients hospitalized in the United States, 31 million (80%) receive an IV catheter for nutrition, medication, and fluids. Obtaining peripheral venous access is complicated by loose tissue, scar tissue from repeat sticks, hypotension, hypovolemic shock, and/or dehydration. These factors manifest in easily collapsed veins, rolling veins, scarred veins, and fragile veins making venipuncture problematic. Most hospitals allow a clinician to make several attempts at peripheral IV access before the hospital "IV team" is called. Studies have shown that success can improve significantly with experience. There are also a number of techniques that can be used such as tourniquets, nitroglycerin ointment, hand/arm warming, but these require additional time, are cumbersome, and do not work effectively in all situations. Tools are also available to improve visualization of the vasculature that use illumination, infrared imaging, or ultrasound. These tools, however, do not simplify peripheral venous access into a collapsible vein. In emergency situations, a clinician will often insert a central venous catheter (CVC) or possibly an intraosseous line. These procedures are more invasive, costly, and higher risk. Multiple needle sticks significantly increase patient anxiety and pain, leading to decreased patient cooperation, vasoconstriction, and greater opportunity for infection and complications. Repeated attempts to obtain venous access are costly to the healthcare facility; estimated at over $200,000 annually for a small hospital. In endoscopy facilities, which see large numbers of older patients, the problem is further exacerbated by fasting requirements that decreases the pressure in the veins. During cannulation, the needle and catheter push the near wall of the vein into the far wall, collapsing the vein—inhibiting the ability to place the needle into the inner lumen of the vein.

Short-term or permanent percutaneous central venous access, such as by catheterization, is sometimes associated with procedures such as hemodialysis, chemotherapy, dialysis, bone marrow transplantation, long-term antibiotic therapy and parenteral nutrition. A common approach to placing a percutaneous central venous catheter (CVC) follows a procedure developed by Swedish radiologist Sven Seldinger in the 1950s. To perform a catheterization of a vessel (e.g., internal jugular vein), a hollow introducer needle is manually advanced through the skin until the near wall of the vessel is punctured, thereby forming a temporary percutaneous tunnel by which to access the vasculature from outside the body. Alternatively, the introducer needle may incorporate a catheter-over-needle (e.g. peripheral IV catheter device), where the catheter portion is left to create the percutaneous tunnel. A guidewire is then typically threaded into the percutaneous tunnel and advanced some distance into the vessel. With the guidewire placed, the introducing needle (or alternately, a peripheral IV catheter device) is then removed by sliding it back over the guidewire, leaving the guidewire in place inside vessel. A CVC catheter (possibly combined with coaxial dilator) is then advanced over the guidewire and into the desired position within the vessel. The guidewire is then removed without disturbing the CVC catheter, which remains in place to provide short term or permanent, or immediate access to the central vasculature for a finite length of time as governed by patient needs and other circumstances.

There are many possible challenges that make it difficult to percutaneously introduce a needle into vessels. For example, a clinician must be able to locate the target vessel by palpating it or possibly with aid of ultrasound using one hand, while the other hand is used to manipulate and advance the introducer needle. For image-guided procedures in particular, coordinating the movements of the needle-guiding hand with the opposite hand used to control the imaging transducer requires great skill, especially to keep the needle identified in the imaging plane. Once the needle is located inside the vessel, it is also easy to inadvertently reposition the needle tip outside of the vessel when the proximal end is manipulated during the process of advancing the guidewire or in some instances during attachment, removal, or manipulation of other devices (e.g., syringes for introducing anesthetics, saline and medication, or for withdrawing blood). Moreover, the insertion force required for penetration of the needle into the desired position may also pose a challenge for controlled placement, and may also lead to tissue deformations that cause the targeted structure to move out of the needle path during advancement.

For example, due to their elasticity and thickness, both skin and venous tissue can vary in the force required to penetrate. Venous penetration is made even more difficult because of the relatively low pressure in the venous system, as well as the higher vessel wall compliance, as compared to the vessels of the arterial system. Low blood pressure in a hypovolemic patient also contributes to the near wall of the vein being collapsed or compressed into the far wall— increasing the risk for a "blown" vessel when both near and far vessel walls are unintentionally penetrated. If the vessel is blown, a hematoma typically forms and the specific site may no longer be suitable for obtaining vascular access and a new location must be selected and the process begun anew. Vasculature is typically smaller in females than in males, compounding the difficulty of blood vessel entry. The needle insertion process, as performed by a skilled clinician, can be impeded due to the lack of surface tension on the vein wall and by the rolling of veins out of the path of the needle upon even slight tangential contact by the needle.

Procedures such as subclavian vein insertion and internal jugular venipuncture are also quite risky due to the force necessary for penetration of a needle into veins and arteries. For example, because the lung apex is close to the clavicle and subclavian vein, the risk of overshooting and causing accidental pneumothorax is increased. To reduce the risk of overshooting, clinicians are advised to insert the introducer needle and then "walk" it slowly against the edge of the collar bone. Since the applied force necessary to produce enough forward momentum to pass the overlying tissues can be relatively high, the procedure must be performed carefully and slowly. Unfortunately, because of this high force, a clinician has little time to react in order to stop the forward momentum immediately after successful venipuncture is achieved. In some cases, by the time a clinician can react to counteract forward momentum following vessel wall puncture, the needle may overshoot and enter the pleural space resulting in a pneumothorax. At this point, advanced emergency intervention by specialized and trained assistants is required. This is just one example of the risks and potential complications of placing a CVC line or other line into a vessel or other location in the body. Another critical complication is that of infection by clinicians breaking sterility, exacerbated when multiple attempts are required to access the vein and/or place a guidewire. Maintaining sterility throughout the procedure is critical.

Tissue deformation during needle insertion is also an issue for soft tissue biopsy of tumors or lesions. Conventional needles tend to deform the tissue during the insertion, which can cause misalignment of the needle path and the target area to be sampled. The amount of tissue deformation can be partially reduced by increasing the needle insertion velocity, and so this property has been exploited by biopsy guns on the market today.

Blood sampling is one of the more common procedures in biomedical research involving laboratory animals, such as mice and rats. A number of techniques and routes for obtaining blood samples exist. Some routes require/recommend anesthesia (such as jugular or retro-orbital), while others do not (such as tail vein/artery, saphenous vein or submandibular vein). All techniques utilize a sharp (lancet, hypodermic needle, or pointed scalpel) that is manually forced into the tissue to produce a puncture that bleeds. A capillary tube is positioned over the puncture site to collect the blood droplets for analysis, or the blood may be collected into a syringe or vacuum vial. Regardless of the sharp used, if an individual is properly trained the procedure can be performed quickly to minimize pain and stress. It is important to minimize stress as this can interfere with blood chemistry analysis, particularly for stress-related hormones. Another much more expensive strategy is to place an indwelling catheter and obtain blood samples in an automated device. However, the catheter cannot be left in over the life span. In addition, the tethering jackets and cables, which must remain in contact with the animal, will likely cause stress. Microneedles can be implanted with highly reduced insertion force and less pain, but may not produce a large enough puncture to yield significant blood for collection and analysis.

Research supports that needle vibration, or oscillation, causes a reduction in needle insertion forces. The increased needle velocity from oscillation results in decreased tissue deformation, energy absorbed, penetration force, and tissue damage. These effects are partly due to the viscoelastic properties of the biological tissue and can be understood through a modified non-linear Kelvin model that captures the force-deformation response of soft tissue. Since internal tissue deformation for viscoelastic bodies is dependent on velocity, increasing the needle insertion speed results in less tissue deformation. The reduced tissue deformation prior to crack extension increases the rate at which energy is released from the crack, and ultimately reduces the force of rupture. The reduction in force and tissue deformation from the increased rate of needle insertion is especially significant in tissues with high water content such as soft tissue. In addition to reducing the forces associated with cutting into tissue, research has also shown that needle oscillation during insertion reduces the frictional forces between the needle and surrounding tissues.

Recently, a number of vibration devices have been marketed that make use of the Gate's Control Theory of Pain. The basic idea is that the neural processing, and therefore perception of pain, can be minimized or eliminated by competing tactile sensations near the area of pain (or potential pain) originates. Vibrational devices may be placed on the skin in attempt to provide "vibrational anesthesia" to an area prior to, or possibly during, a needle insertion event. Research has shown that tissue penetration with lower insertion forces results in reduced pain. The Gate Control Theory of Pain provides theoretical support for the anesthetic effect of vibration. The needle vibration may stimulate non-nociceptive Aβ fibers and inhibit perception of pain and alleviate the sensation of pain at the spinal cord level. In nature, a mosquito vibrates its proboscis at a frequency of 17-400 Hz to reduce pain and improve tissue penetration.

Other vibrating devices directly attach to a needle-carrying syringe and employ non-directional vibration of the needle during insertion. Reports suggest that this type of approach can ease the pain of needle insertion for administering local anesthetic during dental procedures, and to enhance the treatment of patients undergoing sclerotherapy. These non-directed vibration techniques do not allow for precise direct control of the needle tip displacements, and by their nature induce vibrations out of the plane of insertion, which could increase the risk for tissue damage during insertion. Furthermore, existing vibrational devices for improving needle insertion cannot be readily integrated into a control system which would allow for the ability to control and/or maintain the magnitude of needle oscillation during insertion through a wide range of tissue types.

A need still exists to improve the insertion of penetrating members (such as needles, lancets and catheters), by reducing the force required to insert them, causing less tissue deformation, and inducing less pain and stress to the patient, research subject, and clinician/researcher. As such, there remains room for variation and improvement within the art.

SUMMARY

The present invention is directed to a handheld device that provides axially-directed oscillatory motion (also referred to as reciprocating motion) to a detachable penetrating member (such as but not limited to lancets, needles, catheters, biopsy instruments, and vascular entry instruments) at a distal end, for use in procedures such as vascular entry, catheterization and guidewire placement.

Specifically, the present invention addresses an existing need for a CVC introducer system with a penetrating member which is oscillated in an axial direction in short increments and at such a frequency as to reduce the force necessary for puncturing and sliding through tissue, thereby improving insertion control with less tissue deformation and trauma, ultimately producing a higher vessel penetration/access success rate, for subsequent secondary placement of medical devices such as catheters and guidewires.

The device includes a driving actuator that generates reciprocating motion, such as by a voice coil, piezoelectric element or stack, flextensional transducer, or the like. A coupler is provided to transfer the reciprocating motion to a penetrating member, such as a catheter, having open distal and proximal ends. A lumen is defined between the oppositely disposed open ends of the penetrating member, and has a diameter sized to accommodate a guidewire. The device further includes at least one frictional member, such as a wheel(s) or gear(s) that frictionally engages the guidewire and moves the guidewire during placement. A housing may therefore also be provided to include the frictional member(s). The housing also includes a channel, also dimensioned to accommodate the guidewire, and is positioned so as to align the lumen of the penetrating member with the channel of the housing. The lumen and the channel may be continuous or discontinuous. In at least one embodiment, the frictional member(s) is motorized, such as by a guidewire actuator. In other embodiments, the frictional member(s) is manually operated, such as by the thumb or finger of a practitioner using the device.

The reciprocating motion generated by the driving actuator is generated in an axial direction. The penetrating member is therefore reciprocated in an axial direction as a result of the reciprocating motion of the driving actuator. In at least one embodiment, the penetrating member is coaxial with the first actuator, such that they share a common axis and may be considered in-line with each other. In such embodiments, the channel extends through the driving actuator. This channel lines up with and forms a continuous bore with the lumen of the penetrating member, such that a guidewire can be fed into and through the channel, through the lumen and out the distal end of the penetrating member, where it can be positioned at the target site, such as within a blood vessel.

In at least one other embodiment, the penetrating member is axially offset from the driving actuator. The movement of the penetrating member may therefore occur on an axis different from, but preferably parallel to, the axis of the driving actuator generating the reciprocating motion. In such embodiments, the coupler rigidly connects the driving actuator and the penetrating member so as to transfer the reciprocating motion from one axis to the other. Guidewire feeding occurs in the axis of the penetrating member, and may therefore also be offset from the driving actuator.

In at least one embodiment, the penetrating member and housing may be detachable from the remainder of the device, and may be disposable so as to maintain sterility. The remainder of the device, including the driving actuator, may be reusable without sacrificing sterility.

The device comprises at least one linear reciprocating actuator that can be reversibly attached to a penetrating member or other composite system which itself contains a penetrating member, and wherein the driving actuator provides motion to the penetrating member, causing it to reciprocate at small displacements, thereby reducing the force required to penetrate through tissues. Reciprocating motion of the penetrating member facilitates less tissue displacement and drag, enabling, for example, easier access into rolling or collapsed vasculature. Specific applications of the invention include, but are not limited to, penetration of tissues for delivery or removal of bodily fluids, tissues, nutrients, medicines, therapies, and placement or removal of catheters. This device is for inserting penetrating members into the body, including human or animal subjects, for a variety of applications.

The handheld device disclosed may be a driving actuator composed of a handpiece body housing at least one oscillatory linear actuator. The actuator is preferably a voice coil motor (VCM) but may alternatively be implemented with a DC motor, solenoid, piezoelectric actuator, or linear vibration motor disposed within the handpiece body. The linear actuator causes a motor shaft to oscillate or vibrate back and forth relative to the handpiece body, in the axial direction of the shaft. Attached to one end of the shaft is a coupling mechanism which enables reversible attachment of a penetrating member (or to a separate device that already has a penetrating member attached to it).

The need for reversible attachment to a range of penetrating members or separate devices that employ a penetrating member, requires a number of different attachment schemes in order to cause linear, reciprocating motion of the penetrating member. In the preferred embodiment the handheld device has a coupler that enables reversible attachment of Luer-Slip® (slip tip) or Luer-Lok® (Luer lock) style needle or lancet hubs. In another embodiment of the device, a custom connection enables reversible attachment of separate devices with a penetrating member (such as syringe with attached needle or a safety IV-access device) which allows the linear actuator to vibrate the composite system, thereby resulting in reciprocating motion being delivered to the attached penetrating member.

Additional features include embodiments that enable delivery or removal of fluids down the lumen of hollow penetrating members, via side port that allows access to the inner lumen. Tubing that is sufficiently compliant so as not to impede the reciprocating motion of the actuator and penetrating member, is then used to channel fluid from a source, such as a syringe, into the lumen for delivery of medication or other treatments. The side port which accesses the inner lumen of the penetrating member may also enable bodily fluids or tissues to be extracted by applying suction.

Other additional features include embodiments that enable delivery or removal of fluids through a side mounted syringe that oscillates back and forth relative to the handpiece body where the driving actuator is coupled to the syringe and supplies the oscillation or vibration to the syringe. A coupling mechanism is attached to the syringe that enables reversible attachment of a penetrating member (or to a separate device that already has a penetrating member attached to it). This embodiment includes a means to easily accomplish movement of the syringe plunger to a forward or backward position using the same hand which is holding the device for delivery or removal of bodily fluids, tissues, nutrients, medicines, or therapies.

With regard to driving actuators in the handpiece that exhibit resonant behavior, such as the VCM actuator (discussed in embodiments presented below), the invention includes a set of methods by which to optimally operate the device in order to achieve desired oscillation amplitudes throughout the insertion of a penetrating member into target tissues. The resonant peak in the displacement versus frequency response of the driving actuator is influenced greatly by the loading from the tissue that interacts with the penetrating member. The reason for the change in the frequency response is because the penetrating member experiences frictional, inertial, and elastic forces that interact with the driving actuator, and the overall system exhibits an altered frequency response. By operating the device at some frequency above the resonant frequency of the driving actuator in air (for example >⅓ octave, but more optimally near ½ octave), the reciprocating motion can be maintained with very little, if any, damping for penetration of many tissue types.

Alternatively a feedback loop can be constructed by employing a displacement sensor (such as, but not limited to, a linear variable differential transformer (LVDT) to continually monitor displacement and a controller that can continually adjust the operating frequency to keep it near the actual resonance frequency of the coupled system (tissue and driving actuator, coupled via penetrating member). By attempting to keep the operating frequency near resonance of the coupled system, power requirements of the device are greatly reduced. Keeping the system at resonance also mitigates the need to 'overdrive' the system, i.e., drive at a displacement or frequency greater than needed initially, which can contribute to unnecessary heating. The monitoring of the frequency and displacement of the system can also be used to signal the transducer to stop vibration when penetration of the desired tissue is complete.

Another feedback-based method of maintaining near constant oscillatory displacement amplitude during insertion of the penetrating member into variety of tissues, utilizes current control. With this method, the current amplitude supplied to the driving actuator is increased to overcome the damping effects of tissue on the reciprocating penetration member. Again, a displacement sensor can be employed to continually monitor displacement and adjust current amplitude to achieve the target displacement magnitude. Additional methods may deploy a combination of frequency and current control methods by which to maintain displacement. Other methods may not employ feedback but simply anticipate the loading effect of the target tissue and set the operating frequency or current such that optimal displacement amplitude is achieved at some point during the course of tissue penetration. The system may be off resonance when no load is encountered by the penetrating member. However, when the penetrating member penetrates tissue the loading causes the resonance of the system to move closer to the driving frequency such that no adjustments to the driving actuator are needed. In some instances the resonance of the system may be at the driving frequency in the loaded condition. In other arrangements, the driving actuator may be adjusted so that it is on resonance when in a loaded state, and is off resonance during no load conditions. In yet other arrangements, the operating frequency is not at a resonance frequency when in the no load condition, but the operating frequency is closer to the resonance frequency, as compared to the no load resonance frequency, when in the load condition.

The handheld device of the present invention may require an electrical power signal to excite an internal actuator. Upon excitation by the electrical signal, the driving actuator converts the signal into mechanical energy that results in oscillating motion of the penetrating member, such as an attached needle, lancet, epidural catheter, biopsy instrument, or vascular entry instrument.

Additionally the invention with specific control electronics will provide reduction of force as the penetrating member is inserted and/or retracted from the body.

These and other features, aspects and advantages of the present invention will become better understood with reference to the following description and appended claims. The accompanying drawings, which are incorporated in and constitute part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended Figs. in which:

FIG. 1A is a cross-sectional view of the preferred embodiment of the driving actuator handpiece utilizing a reciprocating VCM and LVDT sensor;

FIG. 2A is a side view of the driving actuator handpiece with a Luer-hub style penetrating member attached;

FIG. 2B is a close up view of the Luer-hub style penetrating member coupled to the distal tip of driving actuator handpiece;

FIG. 7B is a side view of the embodiment of FIG. 7A that shows the guide shaft and coupled plunger in a forward position;

FIG. 7C is a side view of an embodiment of FIG. 7A that shows the guide shaft and coupled syringe plunger in a backward position;

FIG. 8A is a side view of an embodiment utilizing a geared slider for movement of the coupled syringe plunger and located in a forward position;

FIG. 8B is a side view of an embodiment utilizing a geared slider for movement of the coupled syringe plunger and located in a back position;

Figure 1B:
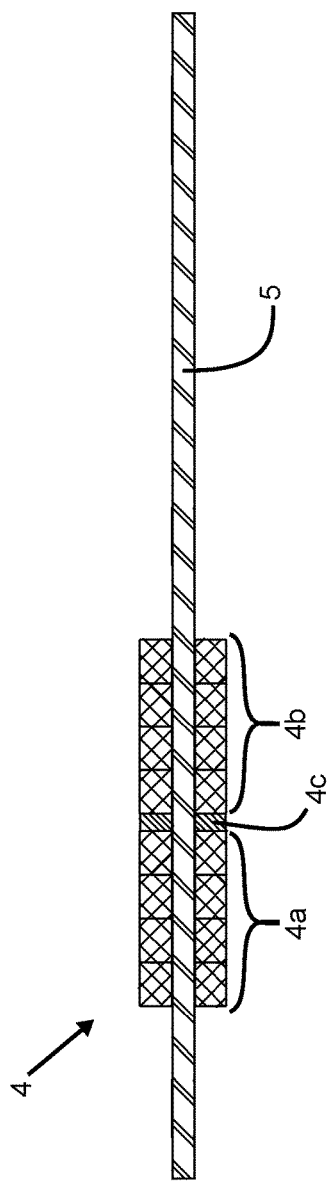
FIG. 1B is a cross-sectional view that illustrates the magnet assembly of the driving actuator (VCM)
Figure 1C:
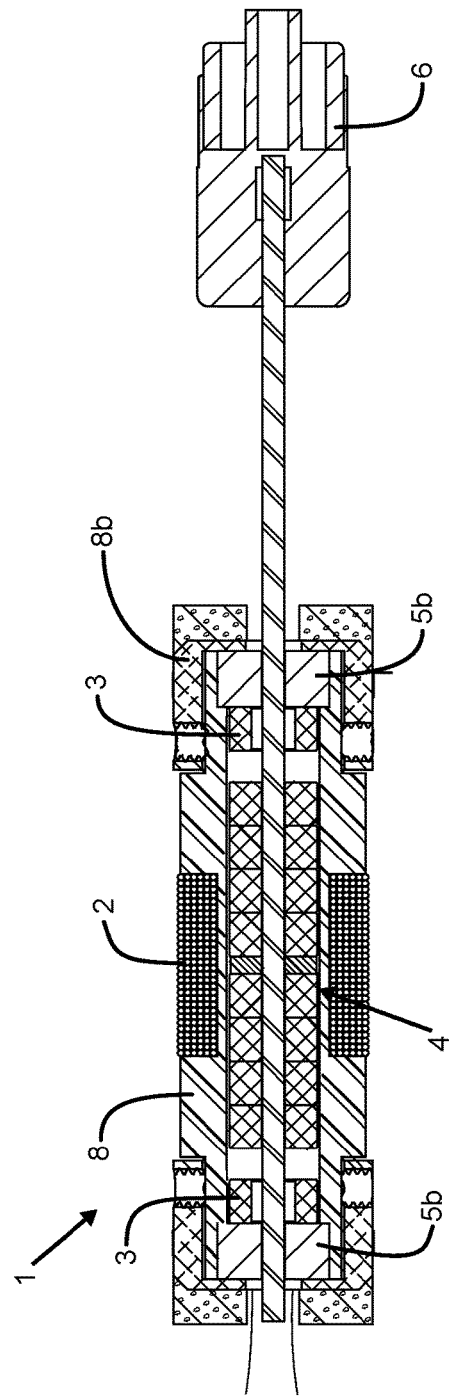
FIG. 1C is a cross-sectional view that illustrates the VCM of FIG. 1A.

Repeat use of reference characters in the present specification and drawings is intended to represent the same or analogous features or elements of the invention.

DETAILED DESCRIPTION

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The contents of U.S. application Ser. No. 14/522,681 filed on Oct. 24, 2014; U.S. application Ser. No. 14/329,177 filed on Jul. 11, 2014; U.S. Pat. No. 8,777,871 issued on Jul. 15, 2014; U.S. Pat. No. 8,328,738 issued on Dec. 11, 2012; U.S. Pat. No. 8,043,229 issued Oct. 25, 2011; U.S. Provisional Application Ser. No. 60/937,749 filed Jun. 29, 2007; U.S. Provisional Application No. 61/089,756 filed Sep. 15, 2008; and U.S. Provisional Application Ser. No. 61/895,789 filed Oct. 25, 2013 are all incorporated by reference herein in their entireties.

The preferred embodiments of the present invention are illustrated in FIGS. 1A-18C with the numerals referring to like and corresponding parts. For purposes of describing relative configuration of various elements of the invention, the terms "distal", "distally", "proximal" or "proximally" are not defined so narrowly as to mean a particular rigid direction, but, rather, are used as placeholders to define relative locations which shall be defined in context with the attached drawings and reference numerals. A listing of the various reference labels are provided at the end of this Specification. In addition, as previously stated U.S. Pat. Nos. 8,043,229 and 8,328,738 were incorporated by reference into the present application and include various embodiments.

The effectiveness of the invention as described, utilizes high-speed oscillatory motion to reduce forces associated with inserting a penetrating member through tissue or materials found within the body. Essentially, when tissue is penetrated by a high speed operation of a penetrating member portion of the device, such as a needle, the force required for entry as well as the amount of tissue deformation is reduced. A reciprocating penetrating member takes advantage of properties of high speed needle insertion, but because the displacement during each oscillatory cycle is small (typically <1 mm) it still enables the ability to maneuver or control the needle, such as to follow a non-linear insertion path or to manual advance the needle to a precise target.

To exploit the reduction of force effect, the medical device of the present invention is designed such that the penetrating distal tip portion attains a short travel distance or displacement at high speed, axially reciprocating at a specified frequency. Utilizing the various device configurations as described in the aforementioned embodiments, it has been determined that the reciprocating motion of the penetrating member may include a displacement for the motor shaft of the driving actuator between 0.1-2 mm, more preferably between 0.5-1.5 mm, and more preferably between 0.2-1 mm, at a frequency of between 50-500 Hz, but most preferably at 75-200 Hz for insertion into soft tissues within the body. This motion is caused by the penetrating member 10 being attached to a voice coil motor operated with an AC power signal.

Generally, any type of motor comprising an actuator assembly, further comprising a voice coil motor (VCM), or solenoid, or any other translational motion device, including piezoelectric actuators, would serve as a driving actuator and also fall within the spirit and scope of the invention.

FIG. 1A depicts an embodiment of the present invention using a linear VCM as the mechanism for the driving actuator 1. FIG. 1A through 3C show cross-sectional view A-A 58, cross-sectional view of the magnet assembly 4, and a detail cross-sectional view of the VCM. A VCM creates low frequency reciprocating motion. In particular, when an alternating electric current is applied through the conducting voice coil 2, the result is a Lorentz Force in a direction defined by a function of the cross-product between the direction of current delivered by the power cable 7 (see FIG. 5) to the voice coil 2 and magnetic field vectors of the magnet arrays 4a and 4b. The two magnet arrays, 4a and 4b, have equal and opposing magnetic polarity vectors and are separated by a pole piece 4c. Together, the magnet arrays 4a, 4b, and pole piece 4c make up the magnet assembly 4. By alternating the direction of the current in the voice coil 2, a sinusoidal alternating force is applied to the magnet assembly 4 resulting in a reciprocating motion of the motor shaft 5 relative to the VCM body 8 which is seated inside the driving actuator handpiece body 1b. The VCM body 8 may be constructed of metal or of plastic with a low coefficient of friction. Delrin is a preferred material choice. The motor shaft bearings 5b provide supplemental friction reduction and help to ensure the motor shaft movement is directed solely in the axial direction (coaxial with the VCM body 8). The reciprocating motor shaft 5 communicates this motion to a keyed coupler 6 and attached penetrating member 10 (see FIG. 2A). The penetrating member 10 may be a hypodermic needle, a solid lancet, or other sharp and may be bonded to a hub 11 (see FIG. 2A) such as, but not limited to a Luer-slip or Luer-lok style. FIG. 2B depicts a close up view of the penetrating member 10 attached via a bonded hub 11 to the keyed coupler 6. The tip of the penetrating member 10 may have a bevel end 12 to increase sharpness.

Referring again to FIG. 1A, in all of the voice coil actuator configurations described, opposite polarity centering magnets 3 may be used to limit and control certain dynamic aspects of the driving actuator 1. At least one centering magnet 3 is located inside the VCM body 8 at each end. The centering magnets 3 have a same inward facing magnetic polarity as the outward facing polarity of the magnet assemblies 4a and 4b; the VCM end caps 8b keep the centering magnets 3 held in place against the repelling force. The opposition of magnetic forces (between centering magnets 3 and magnet assembly 4) acts to keep the magnet assembly centered at the midpoint of the VCM body 8. The magnets are placed at a certain distance from the ends of the magnet arrays 4a and 4b so that they are forced back toward center following peak displacement, but far enough away that no physical contact is made during oscillations. As with other voice coil embodiments using coils, the basic principle of actuation is caused by a time varying magnetic field created inside a solenoidal voice coil 2 when AC current flows in the coil wire, delivered via the power cable 7. The time varying magnetic field acts on the magnet arrays 4a and 4b, each a set of very strong permanent magnets. The entire magnet assembly 4, which is rigidly attached to the motor shaft 5, oscillates back and forth through the voice coil 2. The centering magnets 3 absorb and release energy at each cycle, helping to amplify the oscillating motion experienced by the penetrating member 10 (shown in FIGS. 2A and 2B). The resonant properties of the device can be optimized by magnet selection, number of coil turns in the voice coil 2, mass of the motor shaft 5, and by the elimination of frictional losses as much as possible (e.g. between the magnet assembly 4 and VCM body 8, or between the motor shaft 5 and motor shaft bearings 5b). Furthermore, performance can be optimized by adjusting the strength of the repelling force between the ends of the magnet arrays 4a and 4b and the opposing polarity centering magnets 3, thus modulating the stiffness and overall frequency response of the system. Friction is further eliminated by utilizing a ring style magnet for the centering magnets 3 whose inner diameter is sufficiently larger than the outer diameter of the drive shaft 5. Most application embodiments will require the magnets 3, 4a, and 4c to be made of a Neodymium-Iron-Boron (NdFeB) composition. However other compositions such as, but not limited to Samarium-Cobalt (SmCo), Alnico (AlNiCoCuFe), Strontium Ferrite (SrFeO), or Barium Ferrite (BaFeO) could be used. Slightly weaker magnets could be more optimal in some embodiments, such as a case where the physical size of the system is relatively small and strong magnets would be too powerful.

Feedback means via LVDT 69 and LVDT core 70 can be implemented to monitor oscillatory displacement magnitude, oscillatory frequency, and displacement magnitude from center position. Oscillatory displacement magnitude can be utilized as electromechanical feedback for ensuring the motor shaft 5 is displacing optimally and also potentially can provide a signal that triggers an auto-shut of mechanism. Additionally the LVDT 69 and LVDT core 70 can be used as a force sensor by monitoring the oscillatory center position and comparing it to the unloaded center position. The displacement from center position can be calibrated to relate to a force, since the restoring force provided by the centering magnets 3 increases in proportion to the displacement. This information can be relayed to the operator and/or used as an operating state change trigger.

In some embodiments where larger displacements are desired or a lower resonant frequency is needed, the function of the centering magnets 3 may be replaced with springs, elastic material, and may include a means to dynamically modulate the stiffness of the restoring force or to implement non-symmetric centering forces so that when the penetrating member experiences force from the tissue, the magnet assembly 4 would be located more centrally within the VCM body 8.

One aspect of performing procedures correctly is a manner in which to hold the bevel end (12 in FIG. 2B) of the penetrating member (10 in FIGS. 2A and 2B) rotationally stable. For example, during venipunctures for medication delivery, blood sampling, or for catheterization, a clinician will attempt to locate the tip of a small needle into the center of the vessel. Whether using a lancet or hypodermic needle, the standard technique is to ensure the bevel end (12 in FIG. 2B) of the penetrating member (10 in 2A and FIG. 2B) is "facing up" throughout the penetration event. This is generally not a problem while holding the needle directly in the fingers but needs to be taken into account when the needle is attached to the driving actuator (1 in FIG. 1A). Since the moving magnet assembly (4 in FIG. 1A) does not require leads to be run to the moving part of the motor, as is the case for moving coil actuators, the motor shaft (5 in FIG. 1A) is generally free to rotate within the VCM body (8 in FIG. 1A) meaning that the attached keyed coupler 6 that receives the hub 11 rotates freely. This minimizes frictional losses, but poses a problem for connecting a beveled penetrating member (10 in 2A and FIG. 2B) to the end of the motor shaft (5 in FIG. 1A) because the bevel is not rotationally stable throughout the penetration process. Using springs as the restoring force for centering the magnet assembly (4 in FIG. 1A), supplies some rotationally resistive forces.

Figure 3B:
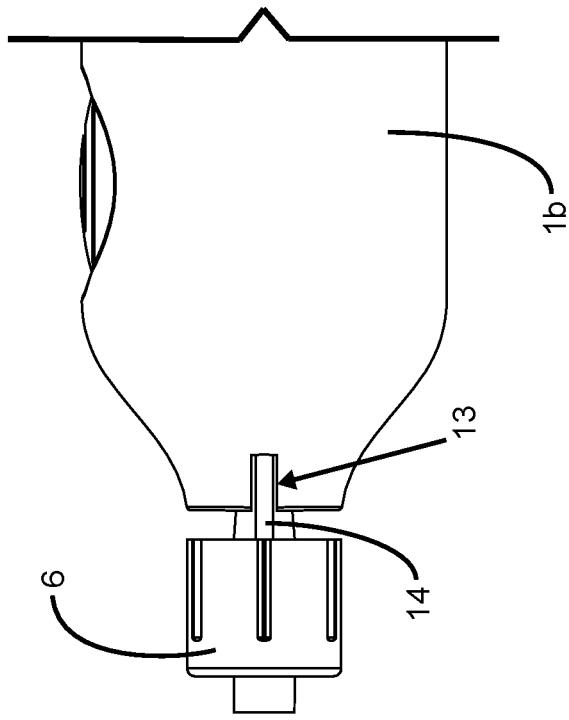
FIG. 3B is a complete side view of the Luer compatible keyed coupler showing the space (keyway) allowed around the tabs (keys) of the coupler.
Figure 3A:
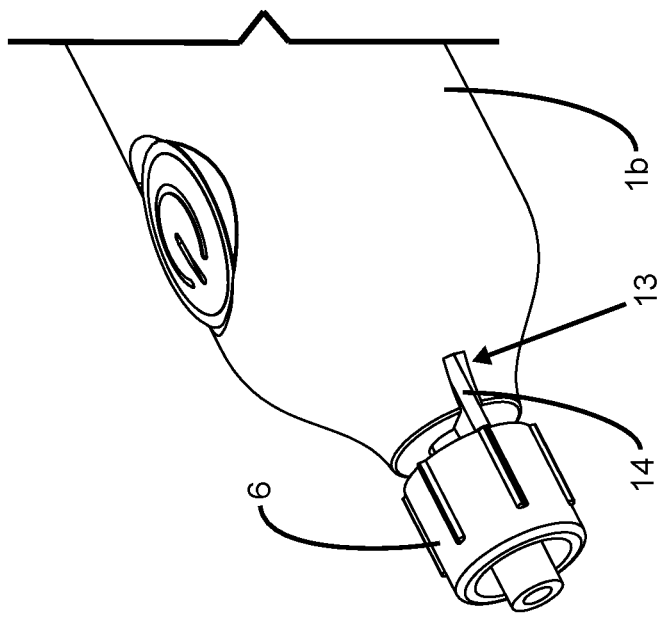
FIG. 3A is a perspective view of the keyed coupler at the distal end of driving actuator handpiece which restricts rotational movement of the attached penetrating member.
Figure 3C:
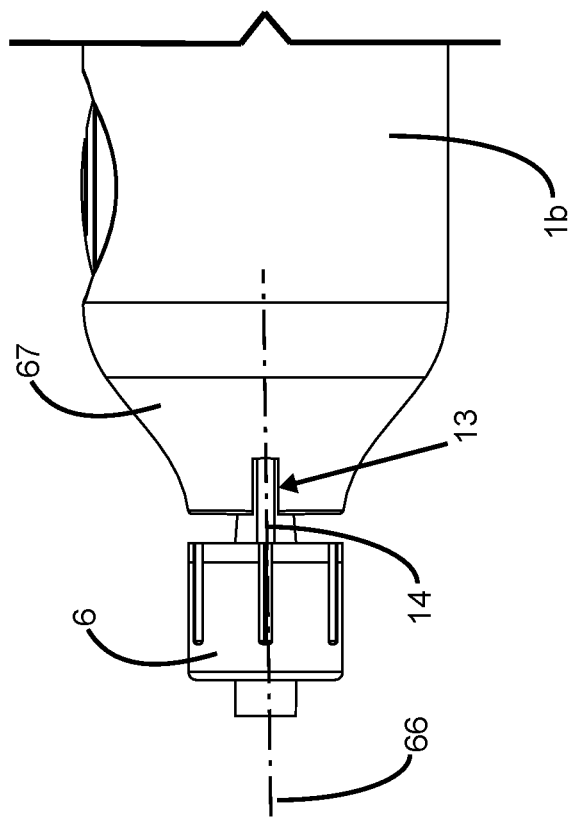
FIG. 3C is a perspective view of the keyed coupler and a rotating keyway head at the distal end of the driving actuator handpiece which provides controlled rotational movement while still allowing axial motion of the attached penetrating member.
Figure 3D:
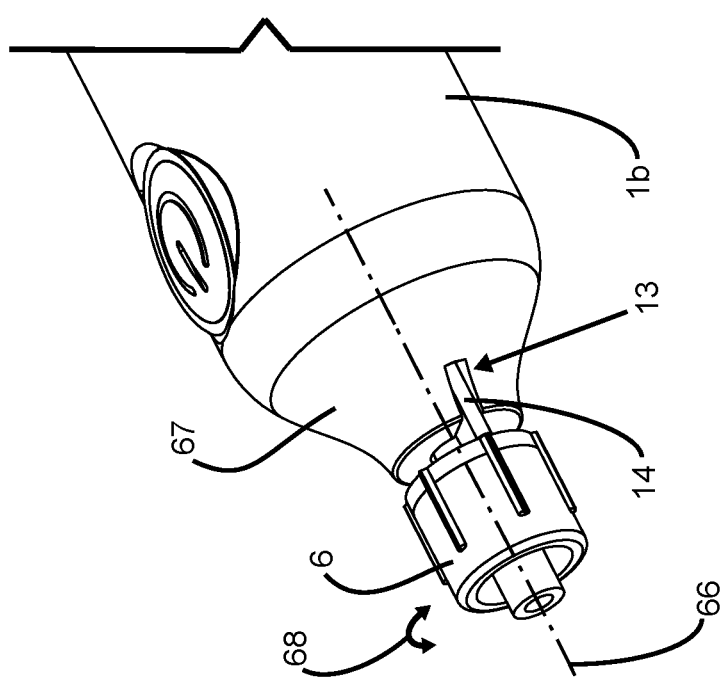
FIG. 3D is a complete side view of the Luer compatible keyed coupler showing the space (keyway) allowed around the tabs (keys) of the coupler within the rotating keyway head.

FIG. 3A presents one approach to restrict axial rotation of penetrating member (10 in FIG. 1C) when attached to the shaft (5 in FIG. 1A). A keyed coupler 6 with side tabs to serve as keys 14 is implemented in conjunction with keyway 13 formed by slots in the distal end of the driving actuator handpiece body 1*b*. The keyed coupler 6 is permanently fixed to the shaft 5 to allow reversible connection, for instance, to Luer-Lok needle hubs, but could be adapted for a range of other attachment schemes. FIG. 3B provides a lateral view of the coupling end of the driving actuator highlighting the keyed coupler 6 and surrounding keyway 13. Sufficient clearance between the keyway 13 slots on either side of the handpiece body 1*b* and the keys 14 is made to prevent frictional forces from damping out the oscillating motion. Friction can further be reduced between the keys 14 and keyway 13 by coatings and/or lining opposing surfaces with low friction materials. In an alternate embodiment depicted in FIGS. 3C and 3D, the front of the device incorporates a rotating keyway head 67 which can undergo controlled rotating motion 68 about a central axis of rotation 66. The motion may be produced by coupling the rotating keyway head 67, to rotational motor (not shown) such as a servomotor. This configuration would decouple the rotational and axial motions so that they can be controlled independently. The combined rotational and axial motions may further aid insertion especially into tougher tissues.

Figure 4:
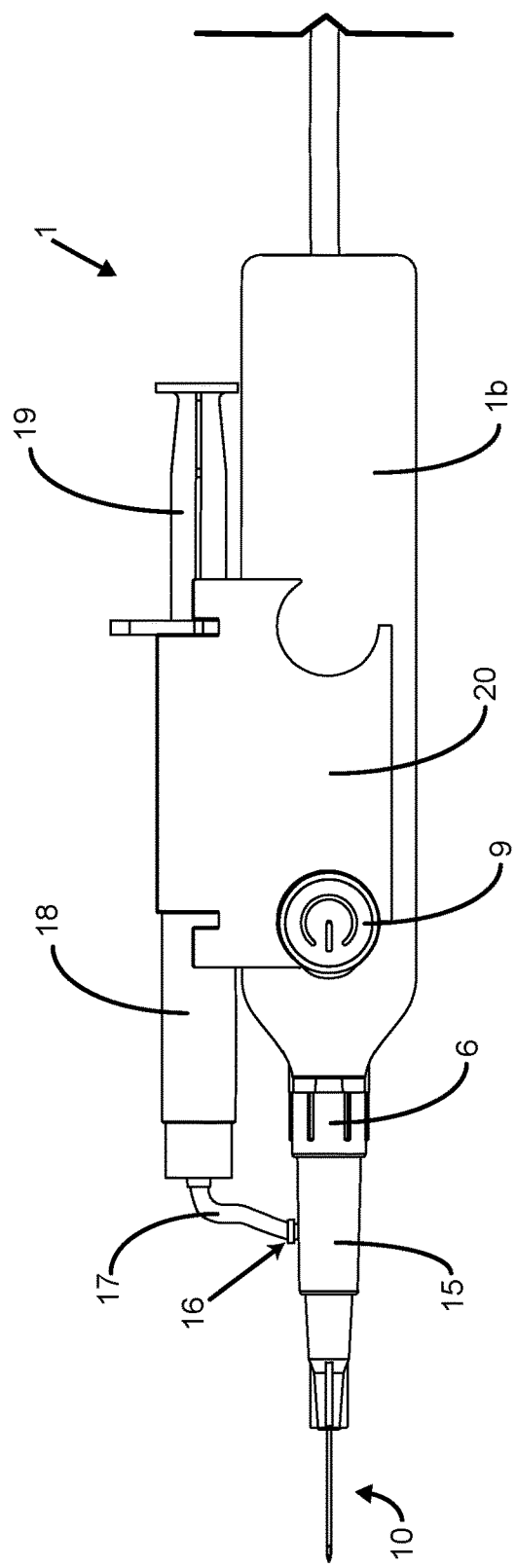
FIG. 4 is a top plane view of the driving actuator handpiece with a mounted syringe connected to the side port of the Luer-hub of penetrating member for removal or injection of fluids.

FIG. 4 shows an alternate embodiment of the device which incorporates a side port 16 which provides access to the inner lumen of the penetrating member 10. A segment of compliant tubing 17 may link the side port 16 to a fluid delivery source such as a syringe. The syringe body 18 can be reversibly attached to the driving actuator handpiece body 1*b* by a syringe coupling bracket 20. When the plunger 19 is pressed into the syringe body 18, fluid (such as medication, fluids, or vaccines,) may be delivered into the body via an inner lumen of the penetrating member 10. In other applications, this or a similar embodiment would allow for extraction of fluids, tissue, or other materials (such as blood, fluid, or cells) into the syringe body 18 by pulling back on the syringe plunger handle 19 to create a negative pressure inside the compliant tubing 17 and inner lumen of the penetrating member 10. The compliant tubing 17 is sufficiently flexible so as not to impede the axially-directed oscillatory motion of the keyed coupler 6 or attached penetrating member 10. Obtaining inner lumen access may be implemented by attaching an intervening coupling piece with side port 15 between the fixed hub of the penetrating member 10 and the keyed coupler 6 as shown in FIG. 4, it could also be implemented by incorporating a side port directly into the fixed hub of the penetrating member 10. Further, the compliant tubing 17 could either be permanently integrated into the hub or coupling piece, or be an independent component with end fittings that reversibly mate with the side port 16 and syringe body 18. Other similar embodiments are envisioned that include a mounted syringe or other method of fluid injection into a side port 16, including gun-style injectors of vaccines and other medications for care and treatment of livestock in agricultural settings.

Figure 5:
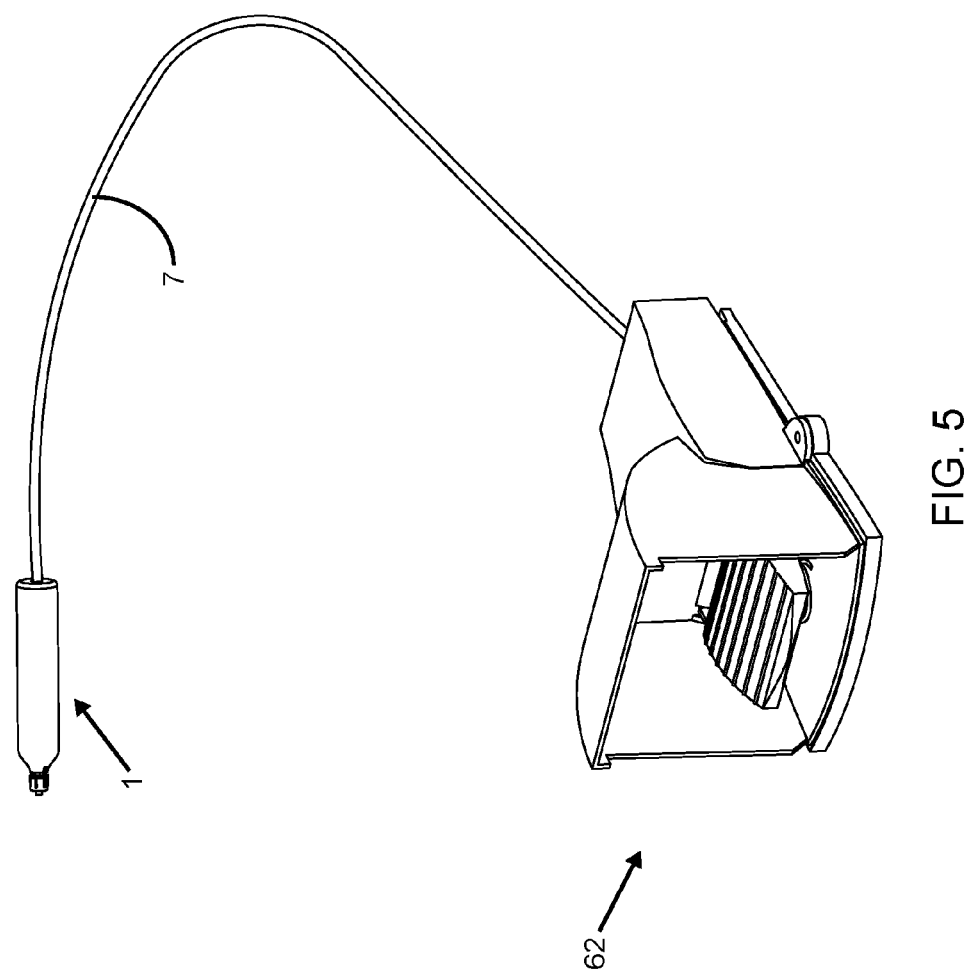
FIG. 5 is a perspective view of the driving actuator handpiece with an incorporated foot switch for initiating and terminating power to the driving actuator.

FIG. 5 presents another approach through use of a foot switch 62, to initialize and de-initialize power supplied to the driving actuator 1 via the power cable 7. This approach can also incorporate both the foot switch 62 and the power button 9 (not shown) for the option of initializing and de-initializing power to the driving actuator 1.

Figure 6A:
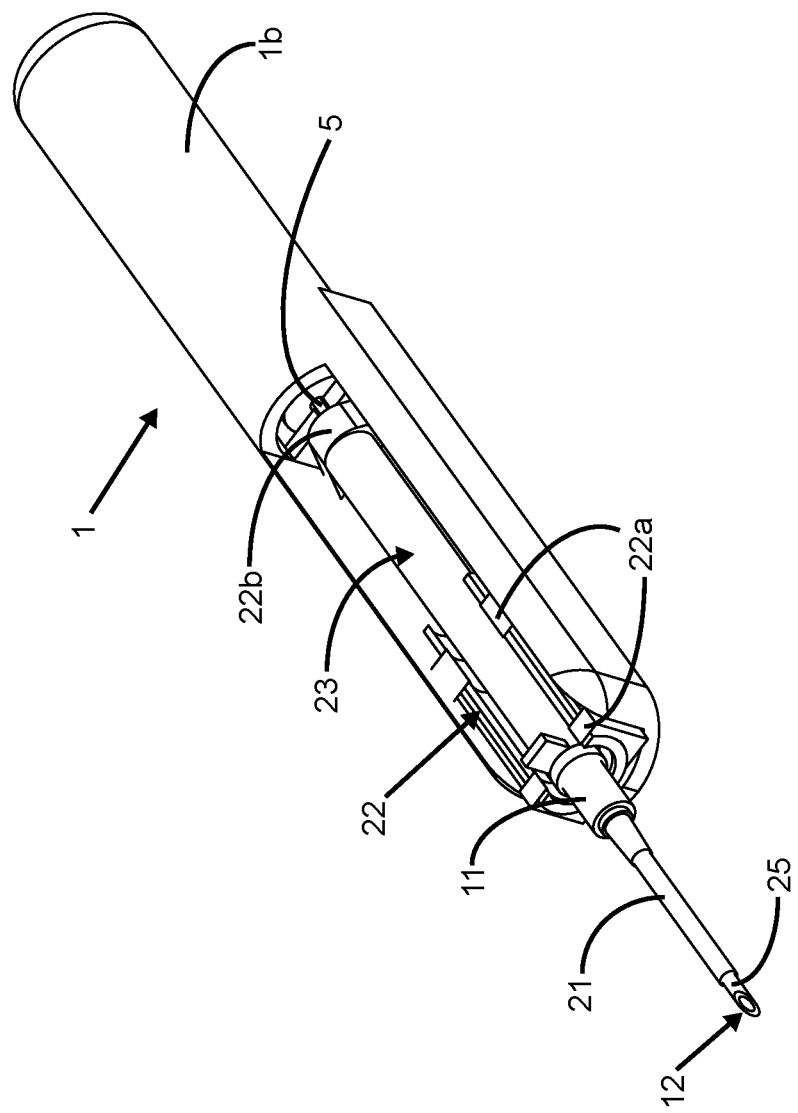
FIG. 6A is a view of an embodiment of the driving actuator handpiece with an inline coupling sled attachment clipped to a safety IV device for the purpose of providing reciprocating motion to penetrating member.
Figures 6B, 6C:
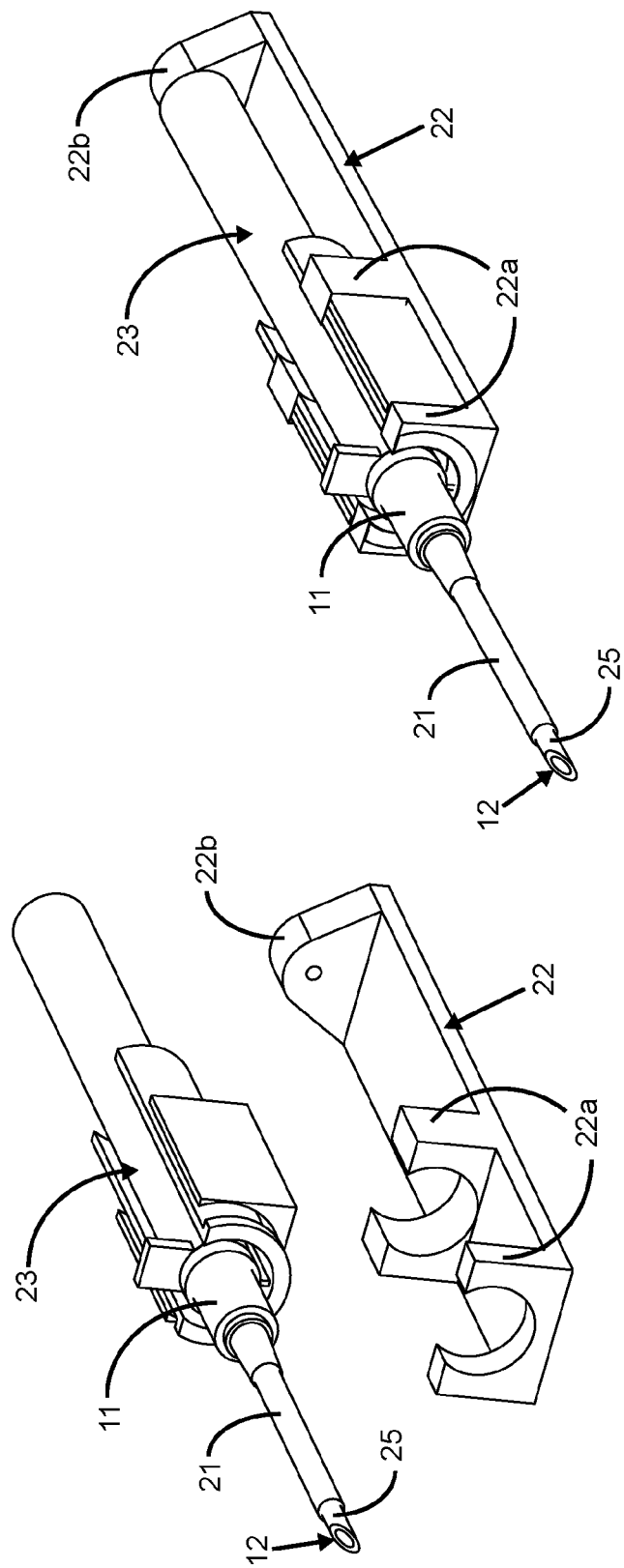
FIG. 6B shows an isolated view demonstrating safety IV device attachment to coupling sled (driving actuator handpiece not shown)
FIG. 6C is a perspective view of the safety IV device after attached to the coupling sled.
Figure 6D:
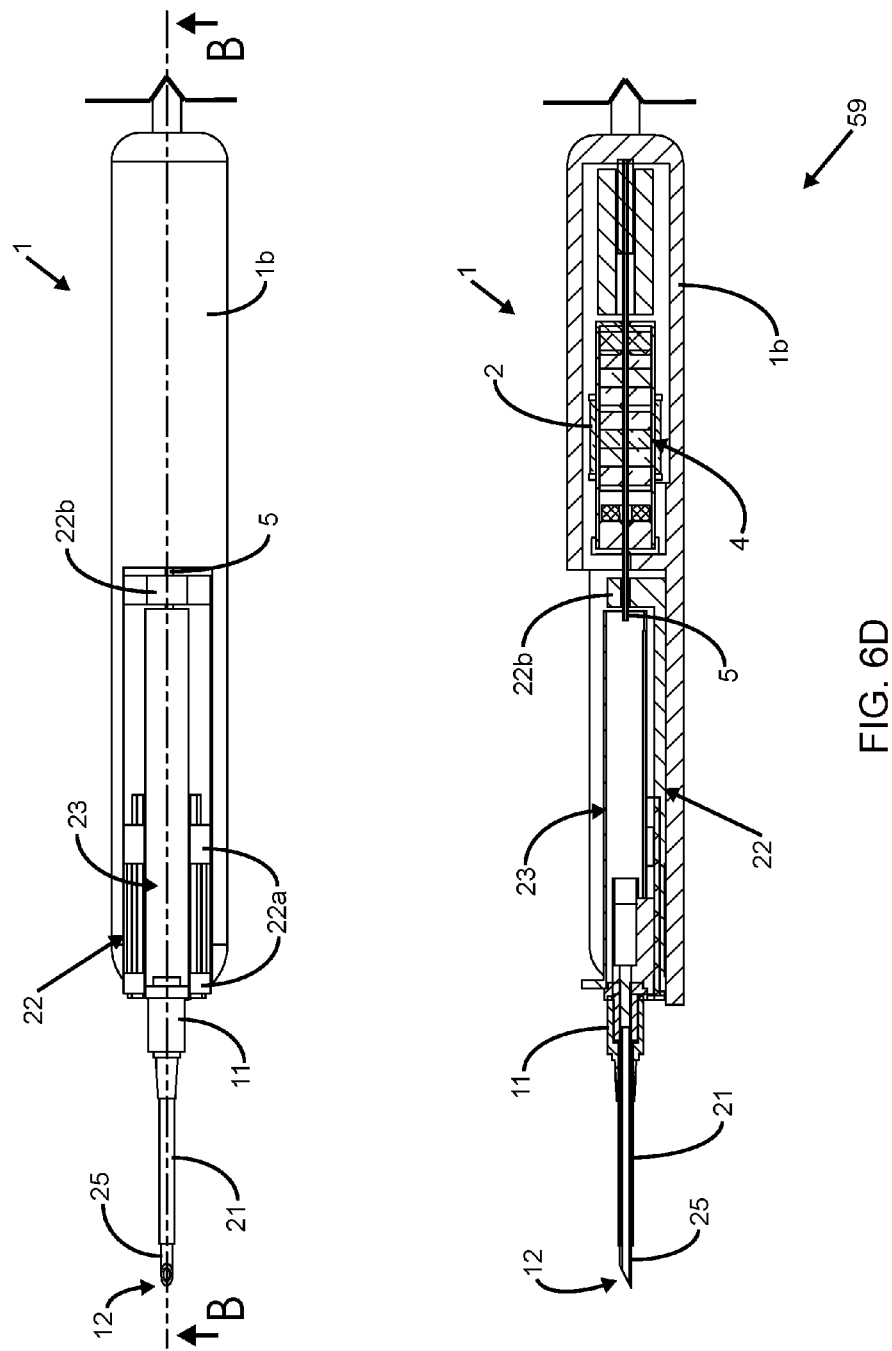
FIG. 6D is a cross-sectional view that illustrates the driving actuator handpiece utilizing a reciprocating VCM that incorporates a coupling sled attachment clipped to a safety IV device.

In another embodiment as shown in FIG. 6A-6D, the driving actuator 1 is used to aid the placement of an IV catheter into a vessel in order to have long-term access to the vascular system. This could be done by using a safety IV device 23 or any other device with an attached penetrating member that does not have a hub that can be easily attached to the driving actuator 1. In this case the driving actuator 1 must be adapted to couple the motor shaft 5 to the body of the penetrating device. This requires the coupling to occur more from the lateral aspect of the device to be oscillated, rather than at the proximal end because a hub is not present or is inaccessible. To accomplish this, a coupling sled 22 (shown in more detail in FIGS. 6B and 6C) that has clips 22*a* that are geometrically compatible with specific penetrating devices is used to attach the penetrating device to the reciprocating motor shaft 5. The proximal end of coupling sled 22*b* connects to the motor shaft 5 which is forced back and forth by the interaction of the magnet assembly 4 and the magnetic field generated by electric current flowing through the voice coil 2. The coupling sled 22 is supported and guided by the structure of the handpiece body 1*b*. During a vascular access procedure, for instance, the driving actuator 1 delivers oscillatory motion to the IV penetrating member 25 to aid tissue penetration. When the bevel end 12 is inside the vessel to be catheterized, the IV catheter 21 is slid off the penetrating member 25 and into the vessel. The penetrating member 25 is then retracted into the body of the safety IV device 23, which can be removed from the clips 22*a* of the coupling sled and discarded. In FIG. 6C, the attachment of a safety IV device 23 to the coupling sled 22 is shown in isolation.

To ensure that the oscillatory motion is not over damped by the coupling sled 22, the moving mechanism must have sufficiently small resistance coefficient. In one embodiment the coupling sled is guided solely by the shape of the handpiece body (1*b* in FIG. 6D, section B-B 59). Here the interfacing surfaces are comprised of two materials having a low coefficient of friction. In another embodiment the coupling sled may be guided by for instance a linear ball-bearing guide rail. In another embodiment the coupling sled is capable of attaching to one or more linear round shafts utilizing bearings or material surfaces with low coefficient of friction to minimize sliding resistance.

Figure 7A:
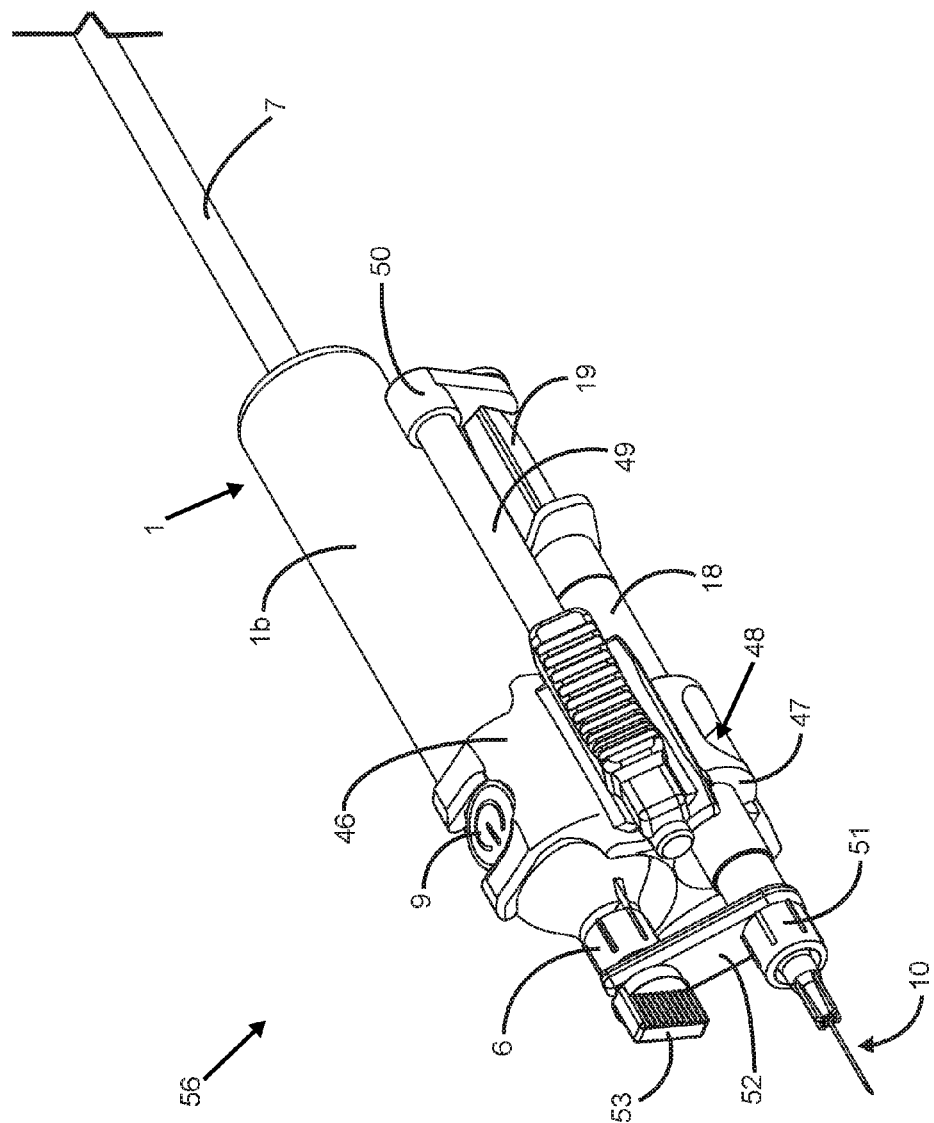
FIG. 7A is a perspective view of an embodiment of the driving actuator handpiece with a side mounted syringe that is attached to the driving actuator to provide axially-directed oscillatory motion to the syringe and coupled penetrating member.

FIG. 7A-7C shows an alternate embodiment, slider device 56, which incorporates a fluid delivery source, such as a syringe, actuated by a driving actuator 1. Power is initialized and de-initialized by the power button 9 and supplied to the driving actuator 1 via the power cable 7. This could also be done with use of a foot switch 62 (as shown in FIG. 5). The actuation is transferred from the driving actuator 1 to the syringe via a keyed coupler 6 and a syringe clip 52. The syringe clip is mechanically attached to the keyed coupler 6 by use of a Luer-Lok coupling member (such as a thumb coupler 53). The syringe clip 52 pivots around the thumb coupler 53 360° to allow for quick attachment and detachment to the syringe coupler 51 which provides a mechanical attachment to both the syringe body 18 and the penetrating member 10. The syringe body 18 can be reversibly attached to the driving actuator handpiece body 1*b* by a handpiece clip 46. The syringe body 18 could be held in place using an interchangeable syringe adapter 47 that is inserted into a cavity of the handpiece clip 46, allowing for different sizes of the syringe body 18 and allowing for precise linear movement of the syringe body 18 within the syringe adapter

47. A means of visibility such as the syringe adapter window 48 is used to allow for clear visibility of the level of fluid (such as medication, fluids, or vaccines) within the syringe. When the plunger 19 is pressed into the syringe body 18, fluid may be delivered into the body via an inner lumen of the penetrating member 10 that is attached to the syringe body 18 through a syringe coupler 51. One-handed operation of the device can be achieved by allowing movement of the plunger 19 to be initiated through movement of the guide shaft 49 coupled to the plunger 19 through the guide shaft coupling 50. In other applications, this or a similar embodiment would allow for extraction of fluids, tissue, or other materials (such as blood, fluid, or cells) into the syringe body 18 by pulling back on the syringe plunger 19. A switch of the handpiece clip 46 may be located distal to the guide shaft coupling 50 and distal to some or all of the plunger 19. The switch of the handpiece clip 46 may be located adjacent the exterior handpiece body 1b and may allow for easier and more convenient actuation of the plunger 19 during use of the device.

FIG. 7B shows this embodiment with the guide shaft 49 pressing the plunger 19 to a forward position 63 following delivery of fluid contents (or the starting condition for fluid removal procedure). FIG. 7C shows this embodiment with the guide shaft 49 pulling the plunger 19 to a backward position 64 for the purpose of removing fluids (or the starting condition for fluid delivery procedure).

Figure 8C:
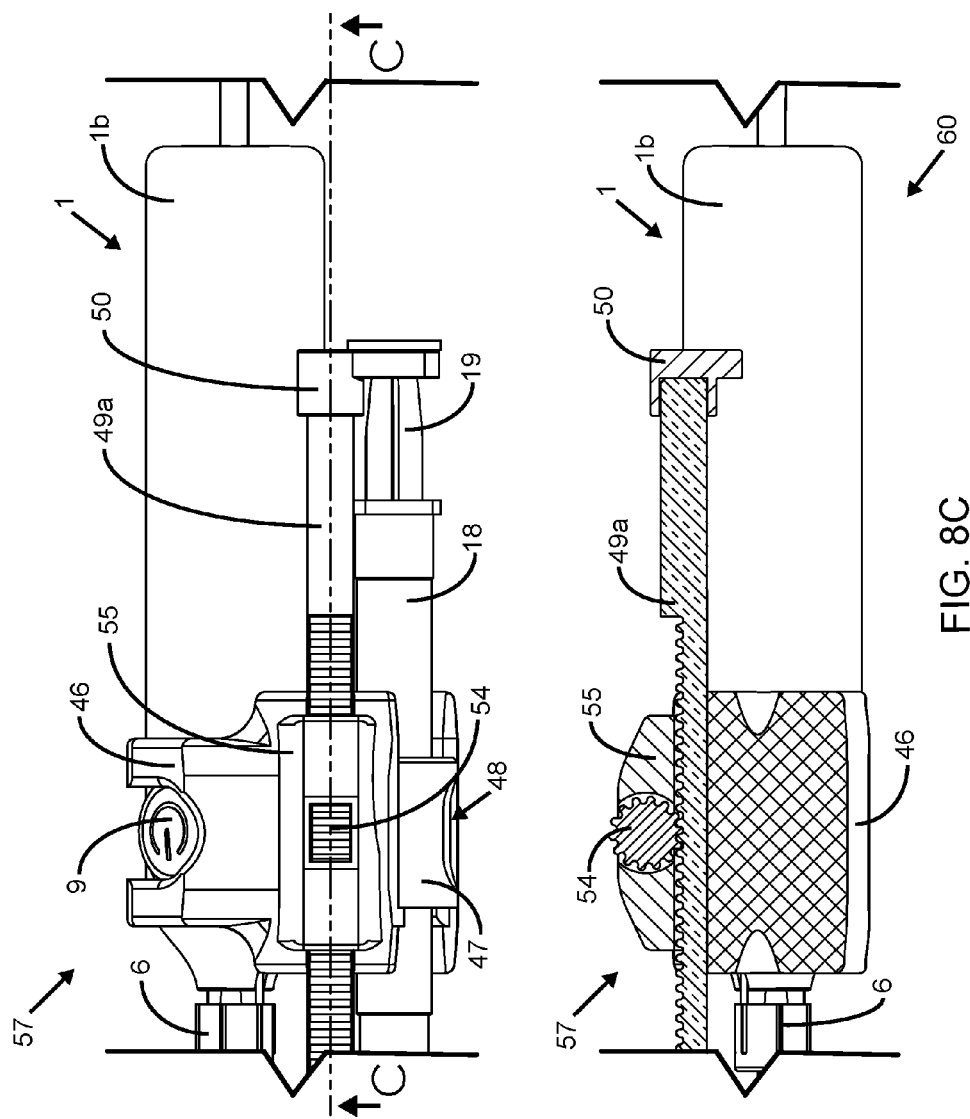
FIG. 8C is a cross-sectional view of an embodiment of FIG. 8A and FIG. 8B utilizing a geared slider to move the coupled syringe plunger forward and back.
Figure 8D:
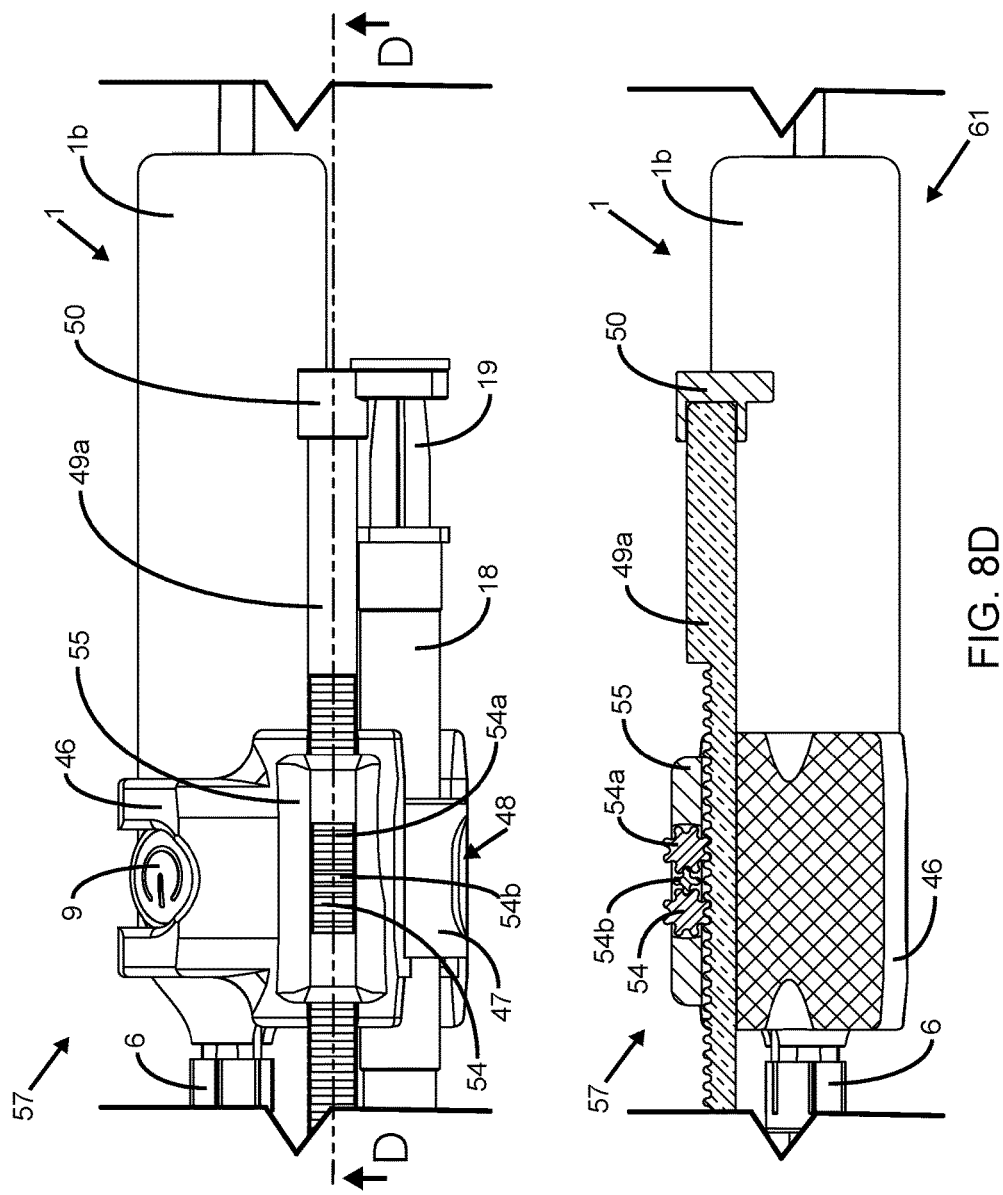
FIG. 8D is a cross-sectional view of an alternate embodiment utilizing a double geared slider to move the coupled syringe plunger forward and back.

FIG. 8A-8C shows an alternate embodiment of FIG. 7A, geared slider device 57, which incorporates a fluid delivery source, such as a syringe, actuated by a driving actuator 1. Power is initialized and de-initialized by the power button 9 and supplied to the driving actuator 1 via the power cable 7. This could also be done with use of a foot switch 62 (as shown in FIG. 5). The actuation is transferred from the driving actuator 1 to the syringe via a keyed coupler 6 and a syringe clip 52. The syringe clip is mechanically attached to the keyed coupler 6 by use of a Luer-Lok coupling member (such as a thumb coupler 53). The syringe clip 52 pivots around the thumb coupler 53 360° to allow for quick attachment and detachment to the syringe coupler 51 which provides the mechanical attachment to both the syringe body 18 and the penetrating member 10. The syringe body 18 can be reversibly attached to the driving actuator handpiece body 1b by a handpiece clip 46. The syringe body 18 could be held in place using an interchangeable syringe adapter 47 that is inserted into a cavity of the handpiece clip 46, allowing for different sizes of the syringe body 18 and allowing for controlled linear movement of the syringe body 18 within the syringe adapter 47. The plunger 19 may move in relation to the handpiece body 1b. A means of visibility such as the syringe adapter window 48 is used to allow for clear visibility of the level of fluid (such as medication, fluids, or vaccines) within the syringe. When the plunger 19 is pressed into the syringe body 18, fluid may be delivered into the body via an inner lumen of the penetrating member 10 that is attached to the syringe body 18 through a syringe coupler 51. Movement of the plunger 19 is initiated through movement of the geared guide shaft 49a and is coupled to the geared guide shaft 49a through the guide shaft coupling 50. A mechanical mechanism including but not limited to a drive gear 54 or a drive gear accompanied by another gear, drive gear two 54a, housed within the drive gear housing 55 can be used to drive the geared guide shaft 49a. The means of providing forward or backward motion to the drive gear 54 or drive gear two 54a is through human kinetic energy or electric energy converted to mechanical energy such as but not limited to a DC motor (not shown). In other applications, this or a similar embodiment would allow for extraction of fluids, tissue, or other materials (such as blood, fluid, or cells) into the syringe body 18 by pulling back on the syringe plunger 19. FIG. 8A shows this embodiment with the geared guide shaft 49a pressing the plunger 19 to a forward position 63 following delivery of fluid contents (or the starting condition for fluid removal procedure). FIG. 8B shows this embodiment with the geared guide shaft 49a pulling the plunger 19 to a backward position 64 for the purpose of removing fluids (or the starting condition for fluid delivery procedure). FIG. 8C shows the geared slider device 57 with the use of a drive gear 54 to move the plunger 19 to a forward position 63 and a back position 64 as shown in FIGS. 8A and 8B. FIG. 8D shows the geared slider device 57 with the use of a drive gear 54 and drive gear two 54a to move the plunger 19 to a forward position 63 and a back position 64 as shown in FIGS. 8A and 8B. If only one gear is turned, drive gear 54 or drive gear two 54a, the other will move simultaneously do to the idler gear 54b along with the interlocking teeth of the geared drive shaft 49a.

Figure 9:
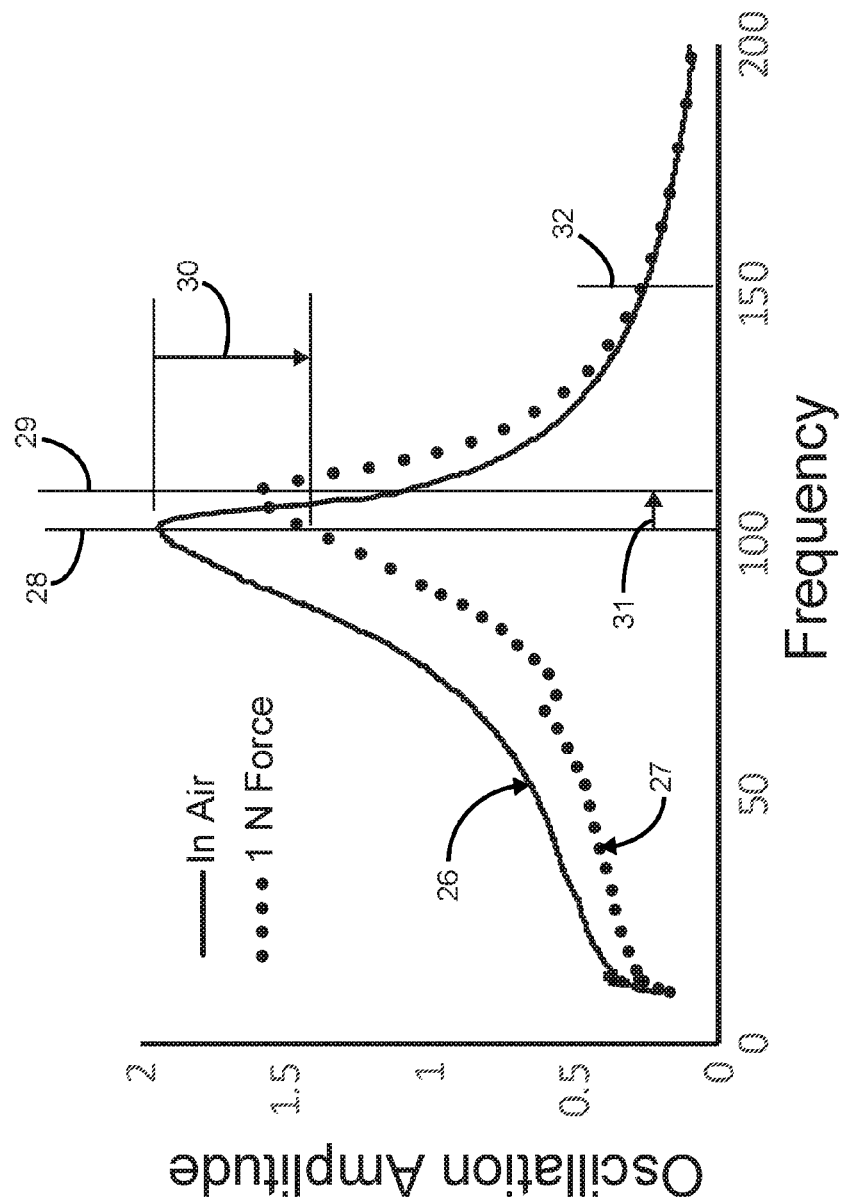
FIG. 9 is a graph showing typical displacement versus frequency behavior for VCM driving actuator in loaded and unloaded conditions.

FIG. 9 displays experimental data obtained with a VCM embodiment of the driving actuator (1 in FIG. 1A) which demonstrates the frequency response behavior of the device as an elastic axial force is applied to keyed coupler 6 (not shown). The frequency response of the driving actuator in air (non-loaded) 26 exhibits resonant behavior with a peak displacement occurring at the resonant frequency in air 28. After the application of a moderate axial load of 1 N (simulating typical forces encountered during penetration of a 25 G hypodermic needle into rat tail skin), the device resonant frequency shifts 31 according to the new frequency response of driving actuator with axial force applied 27 (1 N elastic load force, applied axially). If the device were for instance operated at the original resonant frequency in air 28 when axial load force is applied during the course of tissue penetration, then it would cause an upward resonant frequency shift 31 with a resultant oscillatory displacement damping 30 at original resonant frequency 28. One method to overcome this shortcoming is to choose a damping resistant operating frequency 32 that is significantly higher than the original resonant frequency in air 28. As shown by the plots in FIG. 9, the damping effect of axial load on the oscillatory displacement amplitude is minimal at this damping resistant operating frequency 32, as shown by the overlap of the frequency response curves (i.e., frequency response on driving actuator in air (non-loaded) 26 and frequency response of driving actuator with axial force applied (loaded) 27) above this frequency.

Another method of counteracting the oscillatory damping that is caused by the axial force applied to the penetrating member by the tissue is to employ feedback to adjust the operating frequency or current during the penetration. Two different approaches are now mentioned and illustrated with the aid of FIGS. 10A and 10B which show frequency response curves of a simulated 2nd order mass-spring-damper model with parameters chosen to match behavior comparable to driving actuator characterized in FIG. 9. The simulated frequency response in air 33 of a VCM-based driving actuator in air (non-loaded condition) has a resonant displacement peak in air 35 occurring at the resonant frequency in air 28. When the effect of elastic tissue interaction with the penetrating member is added to the model (as an increase in spring stiffness), the simulated frequency response in tissue 34 is shifted relative to the original simulated frequency response in air 33. The resonant displacement peak in tissue 37 occurs at a different, in this case higher, resonant frequency in tissue 71. The end result is a displacement in tissue at original resonant frequency 36 that is reduced because the resonant frequency in air 28 is different than the resonant frequency in tissue 71. In an embodiment employing a displacement sensor (e.g. LVDT) to monitor oscillatory displacement of the motor shaft 5 (not shown), the reduced displacement is sensed and the controller would adjust the operating frequency closer to the resonant frequency in tissue 71 so that the displacement would necessarily increase closer to the resonant displacement peak in tissue 37. By employing a feedback loop to continually adjust the operating frequency so that it is always near the current resonant frequency of the combined driving actuator-tissue system, power consumption of the device can be minimized.

Figure 10A:
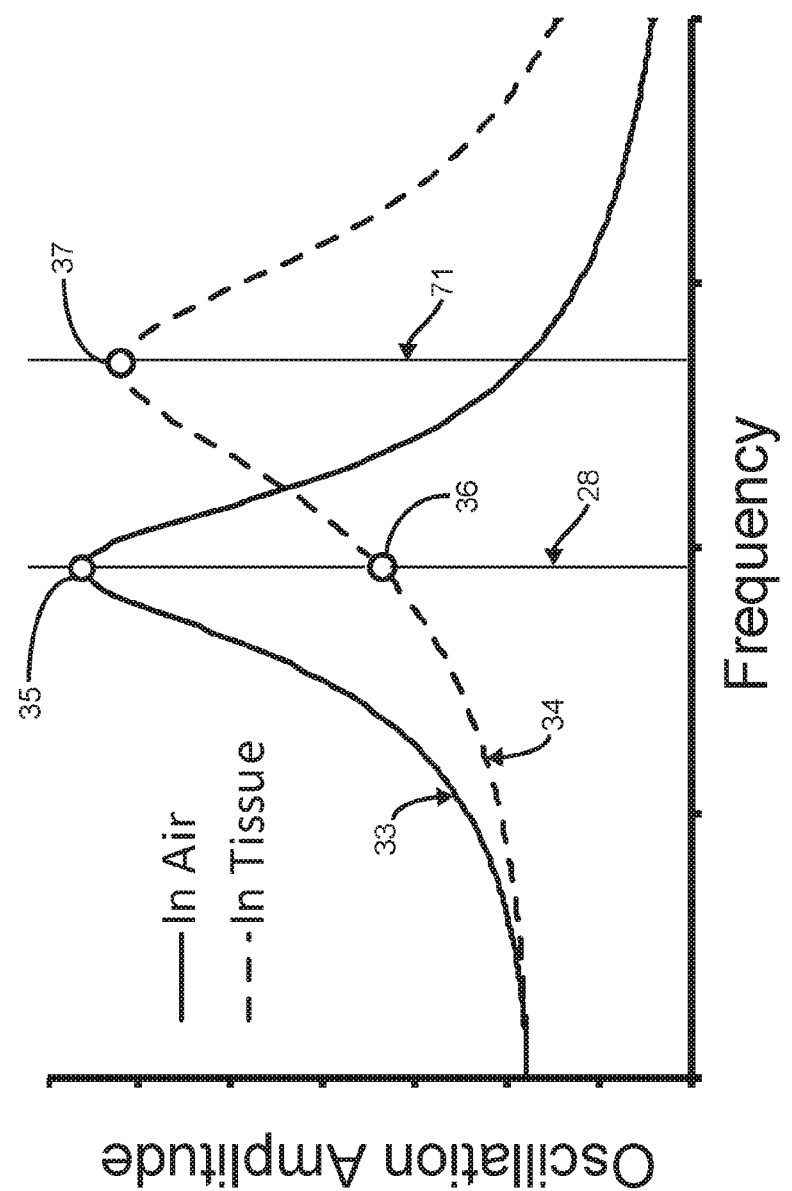
FIG. 10A is a graphic demonstration of frequency-based displacement control method for overcoming the damping effect of tissue during a tissue penetration event using the driving actuator.
Figure 10B:
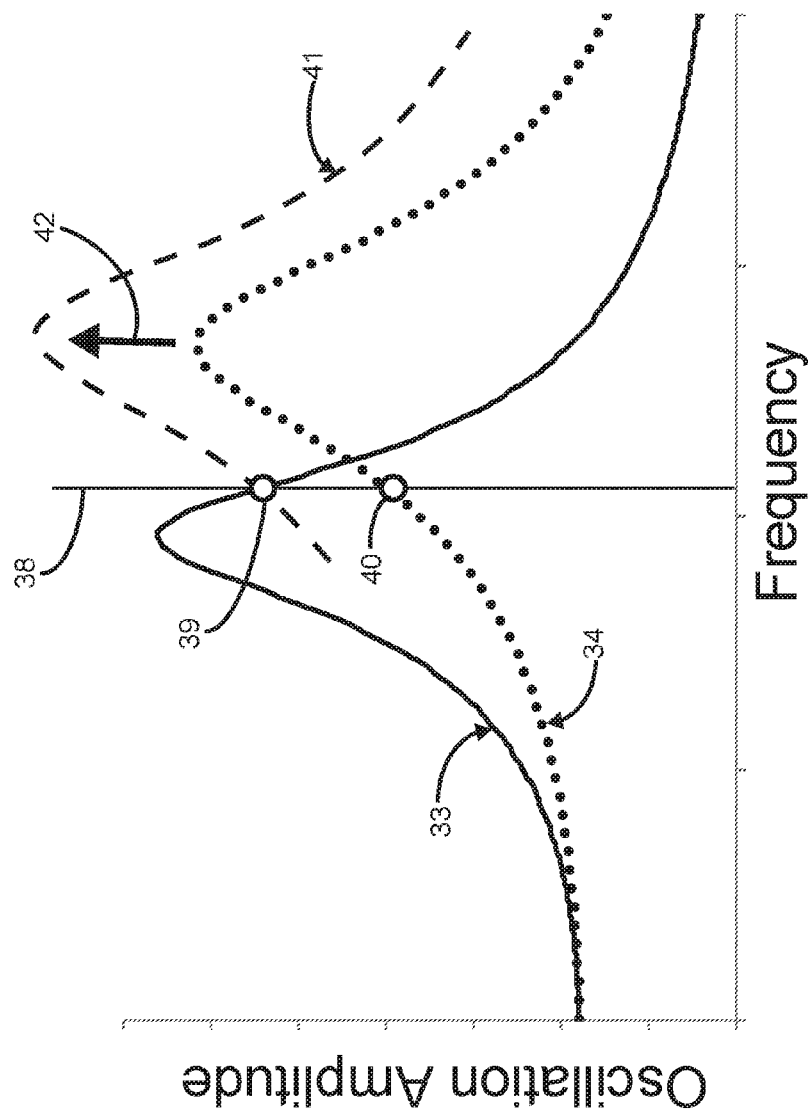
FIG. 10B is a graphic demonstration of a current-based control method for overcoming damping effect of tissue during a tissue penetration event using the driving actuator.

In FIG. 10B, a second method of employing feedback to adjust driving parameters is depicted based on current amplitude control. In this method, current instead of frequency is adjusted during tissue penetration in an attempt to maintain oscillatory displacement levels. As an example, a driving actuator with simulated frequency response in air 33 is driven at the shown operating frequency 38 yielding the oscillatory displacement at operating frequency in air 39. When the penetrating member attached to the driving actuator contacts tissue, the simulated frequency response in tissue 34 may be shifted relative to the simulated frequency response in air 33 as the graph suggests. The shifted simulated frequency response in tissue 34 has reduced displacement at operating frequency after contacting tissue 40 at the operating frequency 38. To counteract the damping of displacement, current amplitude supplied to the driving actuator is increased, resulting in a modified frequency response following increase in current 41, shifted upward as indicated by the arrow 42. Current is increased until the oscillatory displacement reaches the displacement at operating frequency in air 39. At this point the modified frequency response 41 of the coupled system intersects the original simulated frequency response in air 33 at the operating frequency 38, albeit requiring a higher driving current amplitude.

Additional means for maintaining oscillatory displacement level could employ a combination of frequency and current control.

Figure 11:
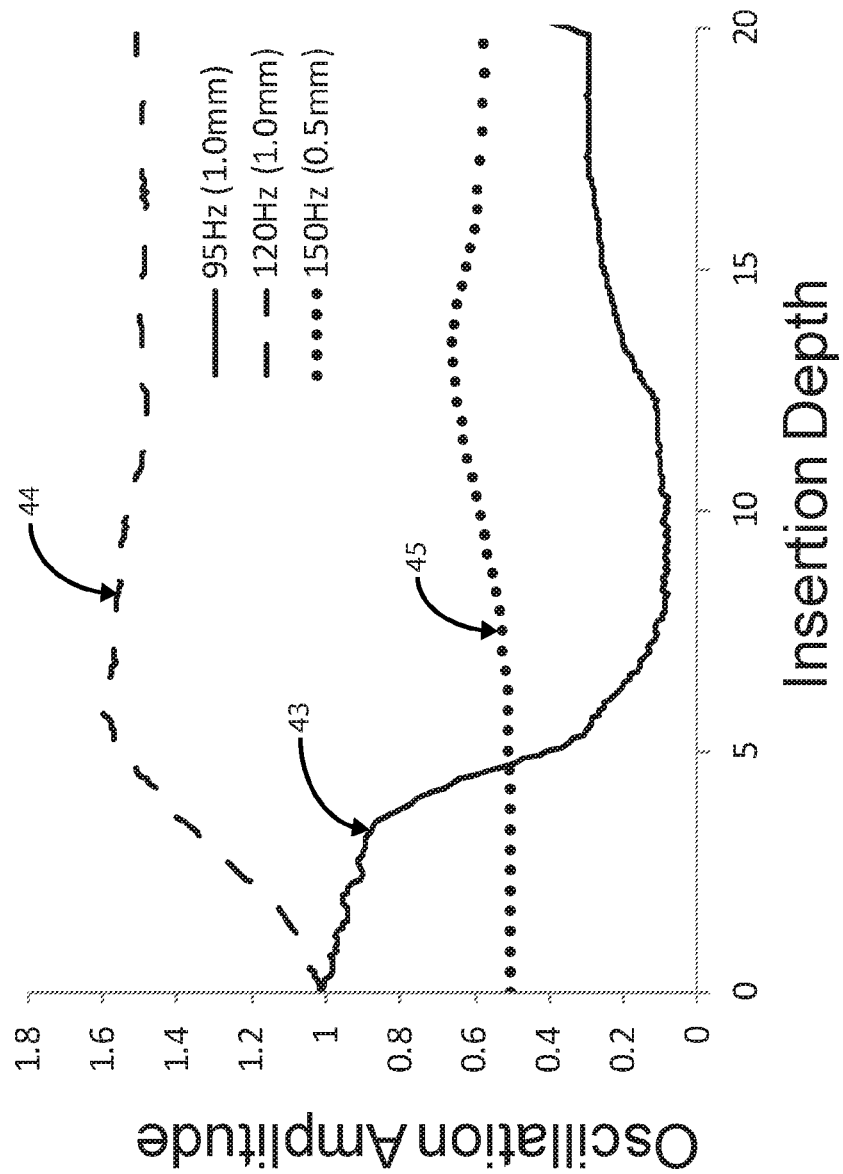
FIG. 11 is a graphic containing plots of displacement (oscillation amplitude) during the course of insertion of a penetrating member into tissue with driving actuator set to provide different displacement frequency and amplitude levels.

FIG. 11 shows the oscillatory displacement amplitude that was measured during insertions into skin tissue at different operating frequency. The resonant frequency of the driving actuator which was used to obtain these curves was near 95 Hz. When the operating frequency was chosen to coincide with the resonant frequency, the oscillatory displacement is damped considerably as shown in the displacement versus insertion depth plot with operating frequency at 95 Hz 43. Choosing an operating frequency of 120 Hz (25 Hz above resonant frequency), the displacement actually increases as the penetrating member contacted and inserted through tissue as shown in displacement versus insertion depth plot with operating frequency at 120 Hz 44. Choosing an even higher operating frequency, the displacement versus insertion depth plot with operating frequency at 150 Hz 45 remained relatively flat. Note: a smaller starting displacement was chosen for plot 45 as compared to plots 43 and 44. Another notable feature with operating at a frequency above the resonance of non-loaded system is that the displacement tends to increase during penetration as the tissue adds axial force to the tip of the penetrating member as seen in plots 44 and 45. When this axial force is removed or reduced, such as when a vessel wall or tissue plane is penetrated, the displacement may decrease, reducing the risk of over penetration. When a feedback loop is employed to control the displacement (see descriptions of FIGS. 6A and 6B), abrupt changes in the axial force (e.g. penetration through a vessel wall) could be sensed by a change in driving characteristics (e.g. power, phase, resonant frequency, oscillation amplitude) to indicate needle tip location (e.g. entry into vessel lumen).

Figure 12:
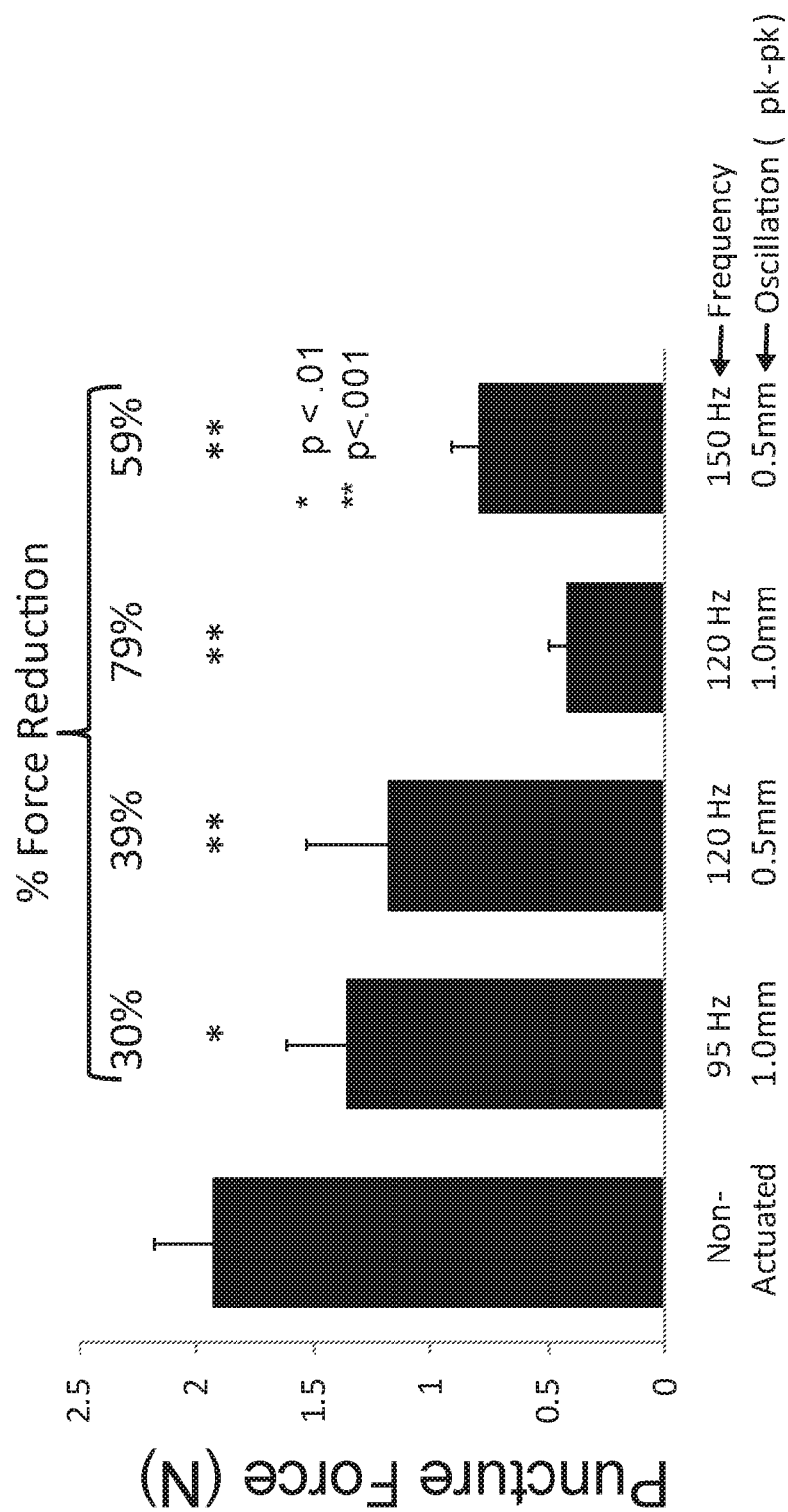
FIG. 12 is a graphical summary of insertion tests of a reciprocated 18G hypodermic needle into porcine skin with the driving actuator delivering different displacement frequency and amplitude levels.

FIG. 12 presents data obtained from insertions into porcine skin with an 18 gauge hypodermic needle serving as the penetrating member. Performance for different operating frequency and starting (in air) oscillatory displacement settings are shown. Depending on the choice of operating parameters, significant force reductions are seen in comparison to insertions of a non-actuated (non-oscillated) needle.

Figure 13:
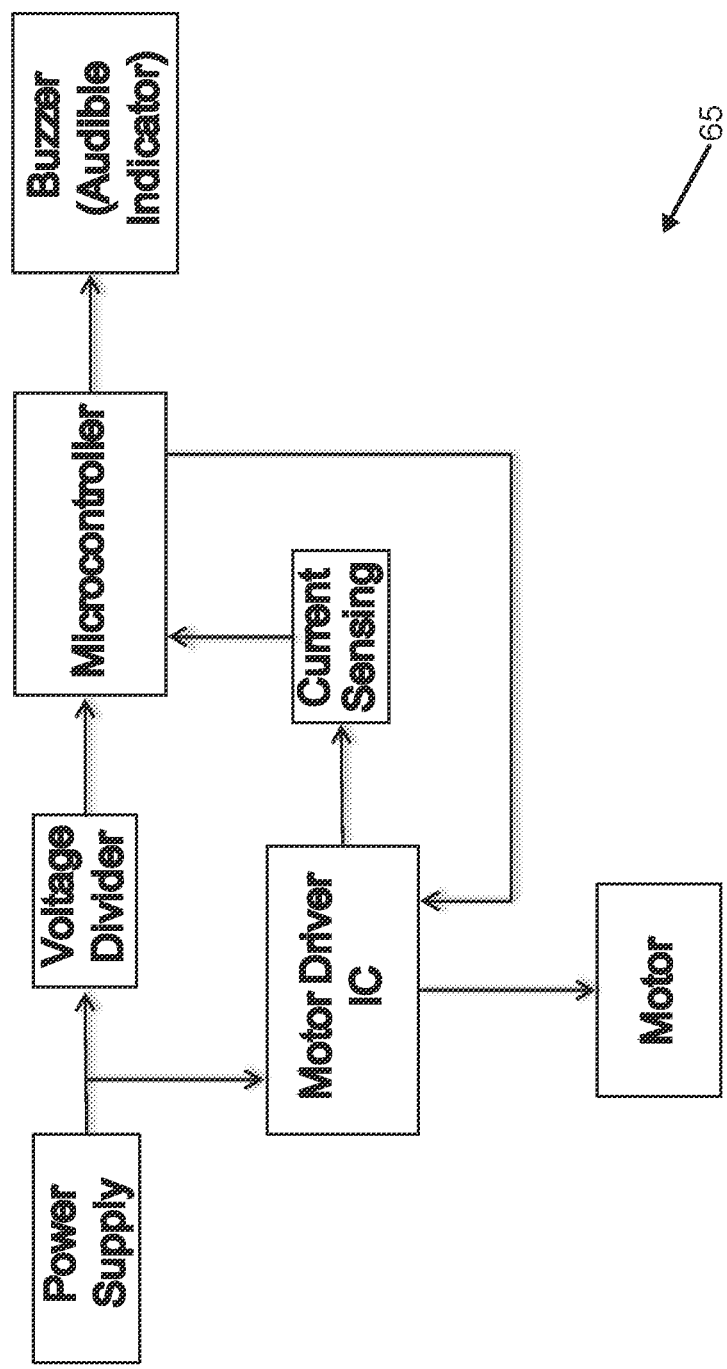
FIG. 13 is a block diagram of electronics layout for voltage and current sensing applications.

FIG. 13 is a control electronics diagram 65 that presents one method of utilizing voltage and current sensing for various control actions. The control electronics employ two sensing methods to ensure that the motor function is operating correctly and to signal the operator if any faults occur. The voltage from the power supply is applied directly to the Motor Driver IC. This voltage is also sensed by the Microcontroller through a Voltage Divider circuit. The Microcontroller monitors this voltage signal and will disable the Motor Driver IC and initiate the Buzzer if the voltage level is outside of a predetermined window. Likewise the Microcontroller also senses and monitors the current through the motor via a current sense pin on the Motor Driver IC. If this current level exceeds a predetermined limit the Microcontroller will disable the Motor Driver IC and initiate the Buzzer. In alternate designs the microcontroller could also be monitoring voltage and current frequency and their relative phase angles.

In the preferred embodiment of the VCM-based driving actuator 1, the VCM coil 2 may be driven by control circuitry such that a constant supply voltage can be applied to the VCM coil 2 at both positive and negative potential or can be turned off to apply zero volts. This supply voltage is switched on and off at a frequency between 10 kHz and 40 kHz where the time that the supply voltage is either 'on' or 'off' can be adjusted. The average voltage seen by the VCM coil 2 over a given switching cycle is proportional to the time the supply voltage is applied. For example, if the supply voltage is applied for 50% of the switching cycle the average voltage seen by the VCM coil 2 will be 50% of the supply voltage. When the VCM coil 2 is supplied with a positive potential voltage a force proportional to the applied voltage will be applied to the magnet assembly 4 of the VCM in one direction while a negative potential voltage will apply a force to the magnet assembly 4 in the opposite direction. By periodically reversing the polarity of the applied potential of the switching signal at 50-500 Hz, an oscillating force can be applied to the motor shaft 5 by way of the attached magnet assembly 4 with an average magnitude proportional to the average voltage magnitude of the generated signal. The energy of this signal will be located at the frequency at which the potential is reversed and every odd multiple of this frequency, the magnitude of which will decrease with each increasing multiple. Likewise, additional energy will also be located at the switching frequency and every odd multiple of this frequency, the magnitude of which will decrease with each increasing multiple.

The frequency response seen in FIGS. 9, 10A and 10B is highly resonant with a weaker response far from the resonant frequency. When the actuator is driven with the described signal where the potential reversal frequency is near resonance, the effects of the energy at higher frequencies is greatly attenuated to the point that they are almost non-existent. This results in a very sinusoidal response without the need for additional filtering or smoothing circuitry. Driving the actuator using this method was chosen because the circuitry necessary to create the signal described is very simple, efficient and cost effective compared to sinusoidal signal generation and is able to take advantage of the physics of the actuator. The ability to use this method is one of the benefits of the VCM design because this method would not be practical to drive an actuator with a wide frequency response when only one frequency of actuation is desired.

In the embodiments of FIGS. 14A-18C, a handheld device is provided for the insertion and placement of a guidewire 75, which can be performed with just one hand. Access to the attached needle or catheter is maintained for introduction of guidewire after successful placement of the needle within a vessel. To avoid dislodging the needle or damaging the surrounding vessel wall, there must be minimal or no manipulation of the needle prior to advancing the guidewire out the distal end of the needle and into the vessel. Since the vibration of the needle is primarily confined to the needle axis, the needle should be parallel to the motion of the vibrational actuator.

Figure 15A:
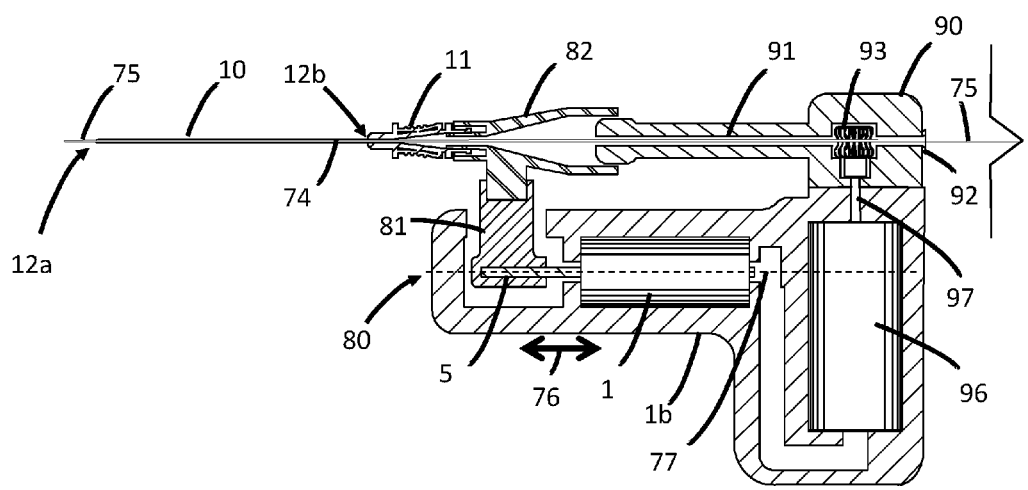
FIG. 15A is a partial cross-section of the embodiment of FIG. 14A.

With particular reference to FIG. 15A, the device includes a driving actuator 1 that generates reciprocating/oscillating motion. As used herein, "reciprocating" and "oscillating" are used interchangeably and refer to a linear axial motion. The driving actuator 1 may be a voice coil motor (VCM), solenoid, DC motor, as described above. In additional embodiments, the driving actuator 1 may be a piezoelectric element or stack, or flextensional transducer.

For instance, in at least one embodiment, the driving actuator 1 is a voice coil motor (VCM) as described previously, and creates a low frequency reciprocating motion. The VCM actuator is more suitable, but not limited, to softer tissue types and is included as a set of methods by which to optimally operate the device in order to achieve desired oscillation amplitudes throughout the insertion of a penetrating member into target tissues. The resonant peak in the displacement versus frequency response of the driving actuator 1 is influenced greatly by the loading from the tissue that interacts with the penetrating member. The reason for the change in the frequency response is because the penetrating member experiences frictional, inertial, and elastic forces that interact with the driving actuator 1, and the overall system exhibits an altered frequency response. By operating the device at some frequency above the resonant frequency of the driving actuator 1 in air (for example >⅓ octave, but more optimally near ½ octave), the reciprocating motion can be maintained with very little, if any, damping.

Voice coil driving actuator 1 creates low frequency reciprocating motion. The voice coil ideally has a bandwidth of approximately 125-175 Hz and a displacement of up to 1 mm that is dependent upon applied AC voltage. In particular, when an alternating electric current is applied through the conducting coil, the result is a Lorentz Force in a direction defined by a function of the cross-product between the direction of current through the conductive coil and magnetic field vectors of the magnetic member. The force results in a reciprocating motion of the magnetic member relative to the coil support tube which is held in place by a body. With the magnetic member fixed to a driving tube, the driving tube communicates this motion to an extension member which in turn communicates motion to the penetrating member 10.

A first attachment point fixes the distal end of the coil support tube to the body. A second attachment point fixes the proximal end of the coil support tube to the body. The conducting coil may be made of different configurations including but not limited to several layers formed by a single wire, several layers formed of different wires either round or other geometric shapes. A first layer of conductive wire is formed by wrapping the wire in a turn-like and spiral fashion and in a radial direction around the coil-support tube with each complete revolution forming a turn next to the previous one and down a first longitudinal direction of the coil support tube. After a predetermined number of turns, an additional layer is formed over the first layer by overlapping a first turn of a second layer of the wire over the last turn of the first layer and, while continuing to wrap the wire in the same radial direction as the first layer, forming a second spiral of wiring with at least the same number of turns as the first layer, each turn formed next to the previous one and in a longitudinal direction opposite to that of the direction in which the first layer was formed. In this embodiment, additional layers may be added by overlapping a first turn of each additional layer of the wire over the last turn of a previous layer and, while continuing to wrap the wire in the same radial direction as the previous layer, forming an additional spiral of wiring with at least the same number of turns as the previous layer, each turn formed next to the previous one and in a longitudinal direction opposite to that of the direction in which the previous layer is formed.

An alternative voice coil configuration could be used where the locations of the magnetic member and conductive coil are switched. In other words, the conductive coil is wrapped around and attached to the driving tube and the magnetic member is located along an outside radius of the coil support tube. An electrical signal of alternating polarity is applied at conductive attachment sites and causes the formation of the Lorentz force to form in an alternating direction that moves the conductive coil and extension member reciprocally along the longitudinal axis of the device.

In all of the voice coil actuator configurations described, springs or pairs of repelling magnets may be used to limit and control certain dynamic aspects of the penetrating member. As with the other voice coil actuators using coils, the basic principle of actuation is caused by a time varying magnetic field created inside a solenoid coil which acts on a set of very strong permanent magnets. The magnets and the entire penetrating member assembly oscillate back and forth through the solenoid coil. The springs (or pairs of repelling magnets) absorb and release energy at each cycle, amplifying the vibration seen at the penetrating member. The resonant properties of the device can be optimized by magnet selection, number of coil turns in the solenoid, mass of the shaft, and the stiffness of the springs.

In at least one other embodiment, the driving actuator 1 includes a piezoelectric element(s), such as transducer(s), for generating reciprocating motion. An embodiment of a piezoelectric version of driving actuator 1 is a Langevin transducer. In this embodiment, when electrically activated, the Langevin transducer transfers compression and expansion of the piezoelectric ceramic portion to a tip of a penetrating member.

Transducer technologies that rely on conventional, single or stacked piezoelectric ceramic assemblies for actuation can be hindered by the maximum strain limit of the piezoelectric materials themselves. Because the maximum strain limit of conventional piezoelectric ceramics is about 0.1% for polycrystalline piezoelectric materials, such as ceramic lead zirconate titanate (PZT) and 0.5% for single crystal piezoelectric materials, it would require a large stack of cells to approach displacement or actuation of several millimeters or even many tens of microns. Using a large stack of cells to actuate components would also require that the medical tool size be increased beyond usable biometric design for handheld instruments. Flextensional transducer assembly designs have been developed which provide amplification in piezoelectric material stack strain displacement. The flextensional designs comprise a piezoelectric material transducer driving cell disposed within a frame, platen, endcaps or housing. The geometry of the frame, platten, endcaps or housing provides amplification of the axial or longitudinal motions of the driver cell to obtain a larger displacement of the flextensional assembly in a particular direction. Essentially, the flextensional transducer assembly more efficiently converts strain in one direction into movement (or force) in a second direction. Flextensional transducers may take on several embodiments.

For example, in one embodiment, flextensional transducers are of the cymbal type, as described in U.S. Pat. No. 5,729,077 (Newnham), which is hereby incorporated by reference. In another embodiment, flextensional transducers are of the amplified piezoelectric actuator ("APA") type as described in U.S. Pat. No. 6,465,936 (Knowles), which is hereby incorporated by reference. In yet another embodiment, the transducer is a Langevin or bolted dumbbell-type transducer, similar to, but not limited to that which is disclosed in United States Patent Application Publication No. 2007/0063618 A1 (Bromfield), which is hereby incorporated by reference.

In another embodiment, the driving actuator 1 includes a flextensional transducer assembly that may utilize flextensional cymbal transducer technology or amplified piezoelectric actuator (APA) transducer technology. The flextensional transducer assembly provides for improved amplification and improved performance, which are above that of a conventional handheld device. For example, the amplification may be improved by up to about 50-fold. Additionally, the flextensional transducer assembly enables handpiece configurations to have a more simplified design and a smaller format.

The various driving actuators 1 of the present invention are connected electrically to an external electrical signal source, such as through a power cable 7. Upon excitation by the electrical signal, the actuator 1 converts the signal into mechanical energy that results in vibratory motion of an end-effector, such as an attached penetrating member, such as a needle or stylet. In the case of a Langevin actuator, the vibratory motion produced by the piezoelectric materials generates a standing wave through the whole assembly Because at a given frequency, a standing wave is comprised of locations of zero-displacement (node, or zero node) and maximum displacement (anti-node) in a continuous manner, the displacement that results at any point along the driving actuator 1 depends on the location where the displacement is to be measured. Therefore, the horn is typically designed with such a length so as to provide the distal end of the horn at an anti-node when the device is operated. In this way, the distal end of the horn experiences a large vibratory displacement in a longitudinal direction with respect to the long axis of the actuator. Conversely, the zero node points are locations best suited for adding port openings or slots so as to make it possible to attach external devices to the actuator.

Regardless of the type, the driving actuator 1 generates reciprocating motion in an axial direction, as shown by directional arrow 76, such as in FIG. 15A. The oscillations produced by the driving actuator 1 are in short increments (such as displacements of up to 1 millimeter) and at such a frequency (such as approximately 125-175 Hz) as to reduce the force necessary for puncturing and sliding through tissue, thereby improving insertion control with less tissue deformation and trauma, ultimately producing a higher vessel penetration/access success rate.

The device further includes a penetrating member 10 connecting to and extending away from the device. As described above, the penetrating member 10 may be a needle, "catheter-over-needle" device, or other similar sharp object for piercing and gaining access to tissue such as skin, muscle, blood vessels, and organs. In at least one embodiment, the penetrating member 10 is a catheter. In at least one other embodiment, the penetrating member 10 is an introducer needle. The penetrating member 10 is elongated in length and defined by an open distal end 12a on one end, and an opposite open proximal end 12b on the other end. The penetrating member 10 extends away from the device such that the distal end 12a may be used to pierce the skin or tissue of a patient, such as for insertion and access to a blood vessel. In at least one embodiment, the distal end 12a may be angled or beveled to increase the ease with which the distal end 12a is inserted. The oppositely disposed proximal end 12b connects the penetrating member 10 to the device, such as through a hub 11 as previously described. The penetrating member 10 attaches securely to the device at the hub 11, and may be releasably attached thereto, such as with a Luer lock fitting or other like connection.

The penetrating member 10 further includes a lumen 74 extending through the penetrating member 10 from the distal end 12a to the proximal end 12b. The lumen 74 is dimensioned to accommodate a guidewire 75, so that the lumen 74 has an inner diameter at least as large as the diameter of a guidewire 75 which is to be inserted therein. For instance, in some embodiments the penetrating member 10 may be between 14 and 18 gauge, while the outer diameter of the guidewire 75 may range of 0.9 to 0.6 millimeters (0.035-0.024 inches). Of course, other sizes and gauges are also contemplated herein.

The device further includes at least one coupler 80 that connects the driving actuator 1 with the penetrating member 10 so as to transmit the reciprocating motion generated by the driving actuator 1 to the penetrating member 10. The coupler 80 may be a single component, or it may be a system of components that coordinate in mechanical communication to transmit the reciprocating motion to the penetrating member 10.

Figure 14A:
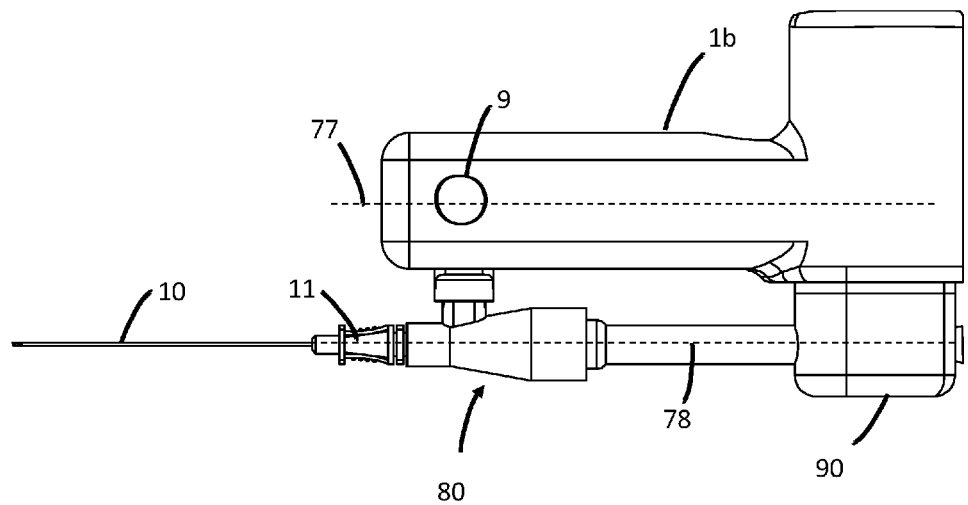
FIG. 14A is a top view of one embodiment of the device showing an axially offset configuration of the penetrating member and first actuator, and a motorized second actuator.
Figure 14B:
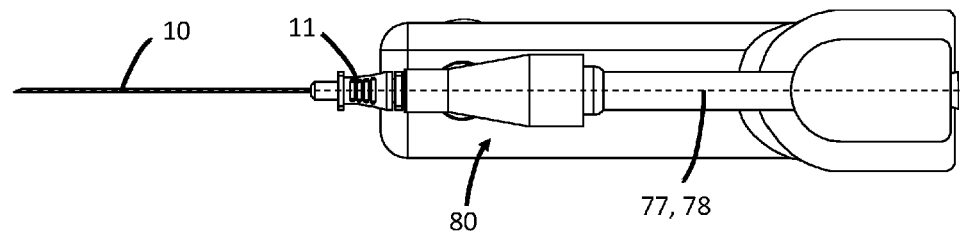
FIG. 14B is a side view of the embodiment of FIG. 14A.

For example, in the embodiments of FIG. 14A-16B, the penetrating member 10 is axially offset from the driving actuator 1. In other words, the axis 77 of vibration of the driving actuator 1 is not collinear with axis 78 of displacement or movement of the penetrating member 10, as depicted in FIG. 14A. These embodiments may be referred to as "offset." In such embodiments, the penetrating member 10 is connected to the device in a manner similar to how a bayonet attaches to a rifle. The axial reciprocating motion generated by the driving actuator 1 must therefore be translated to a different plane or axis for the longitudinal displacement of the penetrating member 10. In a preferred embodiment, as seen in FIG. 14A, the axis 78 of displacement or movement of the penetrating member 10 is parallel to the axis 77 of vibration of the driving actuator 1 as shown in FIG. 15A.

Therefore, in the embodiments of FIGS. 14A-16B, the coupler 80 is a system that connects the driving actuator 1 and penetrating member 10 by spanning the distance between the respective axes 77, 78. For instance, in the embodiment shown in FIG. 15A, the coupler 80 includes a motor shaft 5 extending from the driving actuator 1 along axis 77 in the same axial direction of the reciprocating motion generated by the actuator. The motor shaft 5 may be rigid so to convey the vibrations or oscillations with minimal loss of vibration. Accordingly, the motor shaft 5 also reciprocates in the axial direction.

Opposite of the driving actuator 1, the motor shaft 5 connects to an oscillating coupler 81. The motor shaft 5 may extend into and be at least partially surrounded by the oscillating coupler 81, as shown in FIG. 15A. For example, the motor shaft 5 and oscillating coupler 81 may fit together by lock and groove, or other suitable mating geometry, and may be secured together. In other embodiments, the motor shaft 5 and oscillating coupler 81 attach at their respective peripheral edges. Regardless of how they join, the motor shaft 5 and oscillating coupler 81 are rigidly secured to one another to preserve and faithfully transfer the reciprocating motion from the motor shaft 5 to the oscillating coupler 81. Accordingly, as the motor shaft 5 reciprocates in an axial direction, so too does the oscillating coupler 81 reciprocate.

As seen in FIG. 15A, the oscillating coupler 81 extends away from the motor shaft 5 and connects with an off-axis coupler 82. The oscillating coupler 81 extends away from the axis 77 or plane of vibration of the driving actuator 1, thereby transferring the reciprocating motion to another axis. Accordingly, the oscillating coupler 81 is formed of a rigid material and is rigidly secured to the motor shaft 5 on one end and the off-axis coupler 82 on the opposite end, so as to faithfully transfer the reciprocating motion to the off-axis coupler 82. In turn, the off-axis coupler 82 is connected to the penetrating member 10, which may be a direct connection or connection with the hub 11. The off-axis coupler 82 is in the same axis 78 as the penetrating member 10. Accordingly, as the reciprocating motion is transferred to the off-axis coupler 82, the off-axis coupler 82 conveys this reciprocating motion to the penetrating member 10 along axis 78. This reciprocating motion drives the movement and axial displacement of the penetrating member 10 that avoids the tissue deformation, vein rolling and blown vein complications described above. As a result, the penetrating member 10 oscillates axially parallel to the axial vibrations of the driving actuator 1.

Figure 15B:
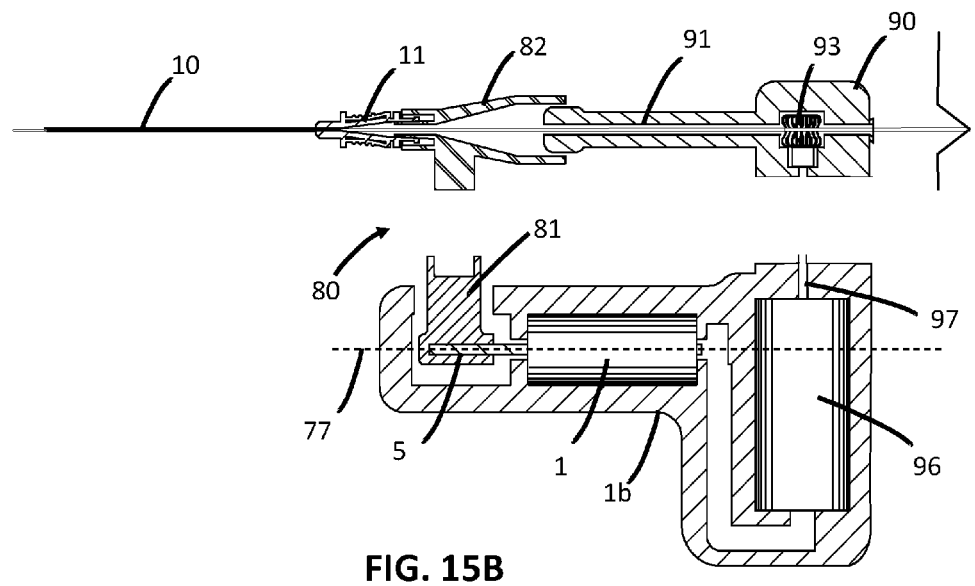
FIG. 15B is an exploded view of the embodiment of FIG. 15A.

In at least one embodiment, the penetrating member 10 and off-axis coupler 82 are selectively connected, so as to be releasable from one another when desired, such as when changing the penetrating member 10 for hygiene. In some embodiments, as in FIG. 15A, the penetrating member 10 may be selectively attached to the hub 11, which may in turn be selectively attached to the off-axis coupler 82. Therefore, the penetrating member 10 itself, or in connection with the hub 11, may be selectively detached from the off-axis coupler 82 when desired. Indeed, in at least one embodiment, the penetrating member 10 may be disposable, intended for one-time use, so as to maintain hygienic conditions. In some embodiments, the off-axis coupler 82 is selectively attached to the oscillating coupler 81, as shown in FIG. 15B, such that the off-axis coupler 82 and penetrating member 10 are disposable, and the oscillating coupler 81, motor shaft 5, and driving actuator 1 are reusable components of the device that can be used subsequently.

Figure 18A:
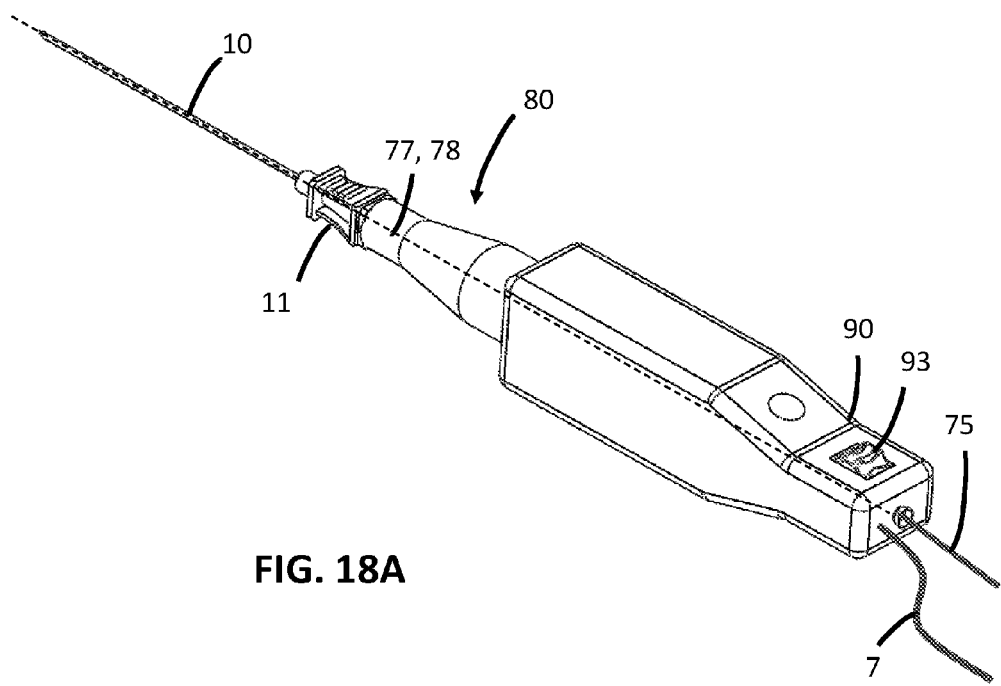
FIG. 18A is a perspective view of one embodiment of the device showing a coaxial configuration of the penetrating member and first actuator.
Figures 18B, 18C:
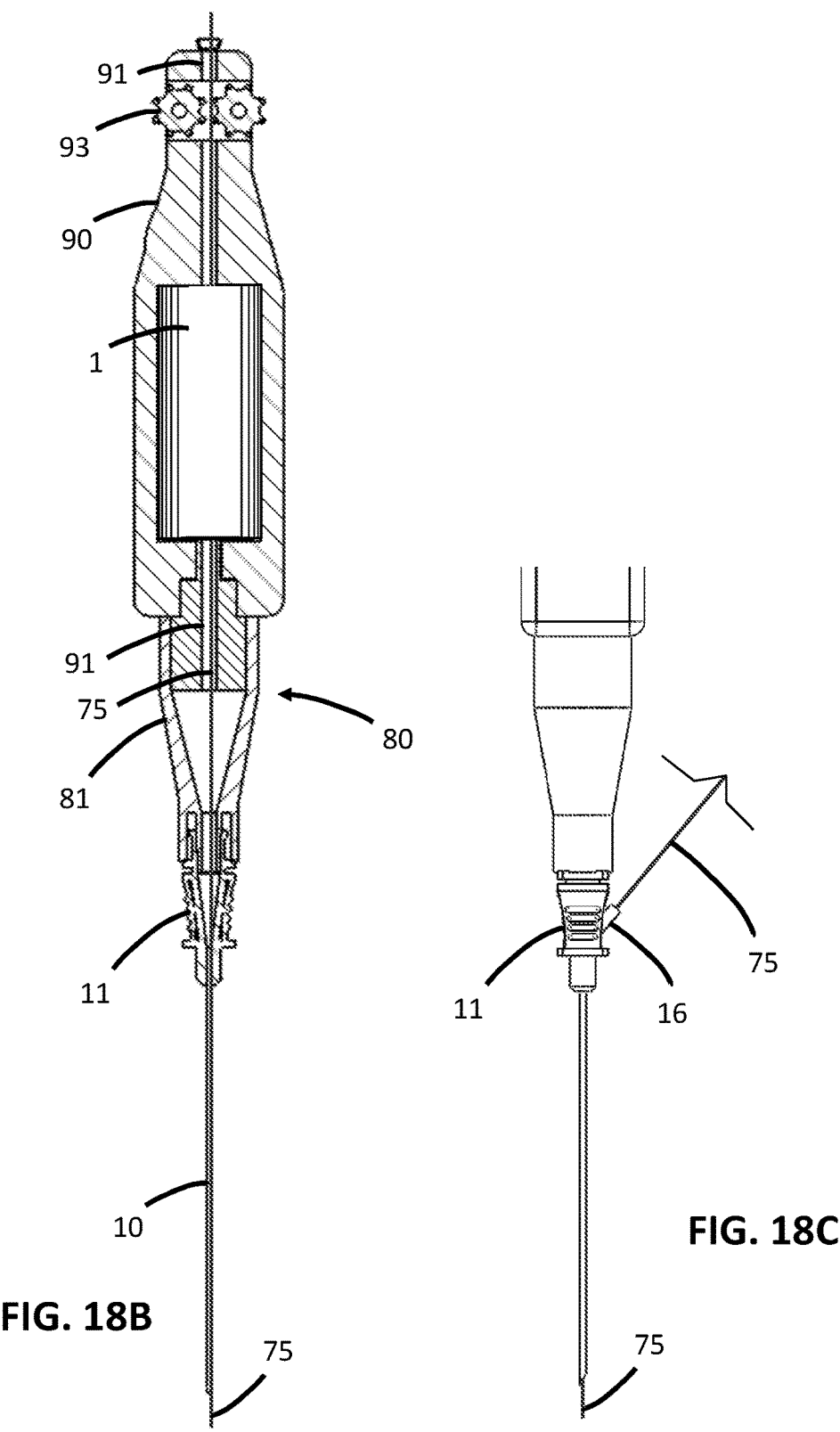
FIG. 18B is a partial cross-section of the embodiment of FIG. 18A.
FIG. 18C is a partial view of an alternate embodiment of the coaxial penetrating member and first actuator device.

In other embodiments, as depicted in FIGS. 18A-18B, the penetrating member 10 is coaxial with the driving actuator 1. Such embodiments may also be referred to as "in-line". In these embodiments, the axis 77 of the driving actuator 1 and the axis 78 of the penetrating member are the same. A coupler 80 transfers the axial reciprocating motion generated by the driving actuator 1 to the penetrating member 10. For instance, in at least one embodiment a motor shaft 5 extends from the driving actuator 1 as described above, and connects to an oscillating coupler 81. Here, the oscillating coupler 81 connects with the penetrating member 10, either directly or through a hub 11 as in FIG. 18B. The reciprocating motion is therefore transferred from the driving actuator 1 through the coupler 80 to the penetrating member 10, all in a common axial direction. In such embodiments, the penetrating member 10 and hub 11 may be selectively attached to the coupler 80, such as oscillating coupler 81, for selective removal in embodiments in which the penetrating member 10 is disposable.

Returning to FIGS. 15A-16B, the device further includes a housing 90 having a channel 91 extending through at least a portion thereof. The channel 91 of the housing 90 aligns with the lumen 74 of the penetrating member 10 along a common linear axis. Like the lumen 74, the channel 91 is dimensioned to accommodate a guidewire 75 there through. In one embodiment, the channel 91 and lumen 74 have the same diameter. In other embodiments, the channel 91 may have a larger or smaller diameter than that of the lumen 74 of the penetrating member. However, the smallest diameter between the lumen 74 and the channel 91 is still sufficiently large to permit passage of the guidewire 75 of intended size there through. Moreover, the channel 91 may maintain the same diameter throughout the housing 90, or it may increase or decrease through portions of the housing 90. For instance, the channel 91 may be larger at the entry point for the guidewire 75, and may taper to a smaller diameter as the channel 91 progresses through the housing 90, so as to align the channel 91 (and thus guidewire 75) with the lumen 74 of the penetrating member for entry therein.

Accordingly, as seen in FIGS. 15A-16B, the housing 90 may be securely attached to at least a portion of the coupler 80, such as the off-axis coupler 82, to bring the channel 91 into alignment with the penetrating member 10. In other embodiments, the housing 90 is flexibly attached to the off-axis coupler 82 so as to allow the penetrating member 10 to reciprocate longitudinally even when the housing 90 is immobile. In still other embodiments, portions of the off-axis coupler 82 may be rigid and other portions flexible, so that the rigid portions may attach to the housing 90 while allowing movement of the flexible portions to permit reciprocating motion to be transferred to the penetrating member 10.

The housing 90 also includes a guidewire port 92 at a peripheral edge or wall, and permits entry of a guidewire 75 into the housing 90. The guidewire port 92 is therefore sized to accommodate the guidewire, and in a preferred embodiment has an inner diameter of similar size to the channel 91. The guidewire port 92 and channel 91 align so that once the guidewire 75 passes through the port 92, it enters the channel 91. Accordingly, the guidewire port 92 may be located opposite of the penetrating member 10. In other embodiments, a guidewire port 92 is not needed, such as when the guidewire 75 is stored coiled or wrapped around a spool within the housing 90, and which is unwound and wound as it is advanced through the channel 91.

In embodiments in which the penetrating member 10 is offset, as in FIGS. 15A-16B, the channel 91 aligns with the axis 78 of the penetrating member 10. In embodiments in which the penetrating member is inline, as in FIGS. 18A-18B, the channel 91 aligns with the axis 78 of the penetrating member 10, which is the same as the axis 77 of the driving actuator 1. Accordingly, the channel 91 also extends through the driving actuator 1 in these embodiments, as shown in FIG. 18B. In an alternate embodiment in which the penetrating member 10 is inline with the driving actuator 1, the guidewire 75 may be inserted through a side port 16 in hub 11, as in FIG. 18C, or may be inserted through a side port 16 in coupler 81. Similarly, the housing 90 that includes the channel 91 may be the same as the handpiece body 1b discussed previously that houses the driving actuator 1. In such embodiments, the voice coil 2 or other elements comprising the driving actuator 1 simply surround the channel 91.

Figure 16A:
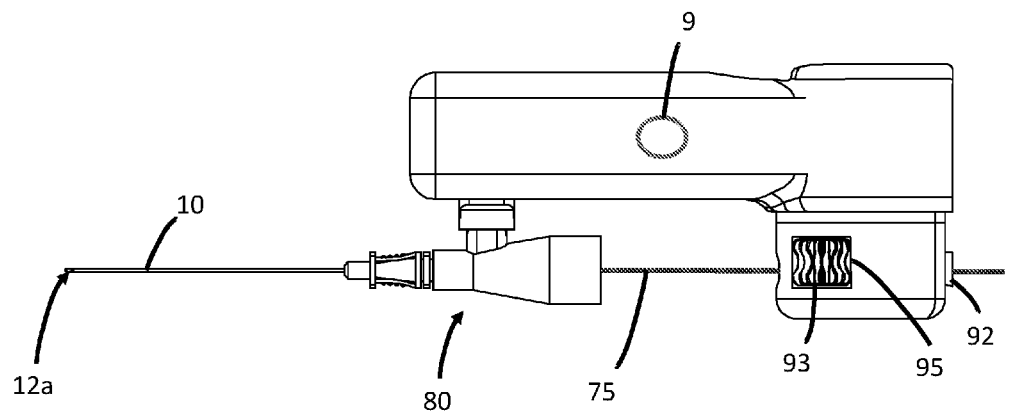
FIG. 16A is a top view of one embodiment of the device showing an axially offset configuration of the penetrating member and first actuator, and a manually operated second actuator.
Figure 16B:
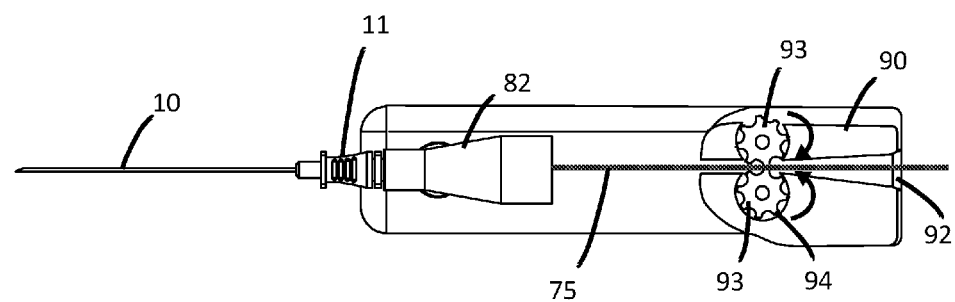
FIG. 16B is a side view of the embodiment of FIG. 16A.

In some embodiments, as shown in FIGS. 15A-15B and 18A-18B, the channel 91 and the lumen 74 are in fluidic engagement with one another and form a continuous bore extending from the guidewire port 92 of the housing 90 to the distal end 12a of the penetrating member 10. In other embodiments, as shown in FIGS. 16A-16B, the channel 91 and lumen 74 are discontinuous with each other but are still aligned along a common axis, such that the guidewire 75 follows a continuous path from the guidewire port 92 in the housing to the distal end 12a of the penetrating member 10.

The device further includes at least one frictional member 93, as seen in FIGS. 15A-16B, 18A, 18B. The frictional member(s) 93 is disposed within the housing 90 and at least partially within the channel 91 so as to engage the guidewire 75. The frictional member(s) 93 is made of a material with a sufficient coefficient of friction so as to grip, pull or push the guidewire 75 when it makes contact with the guidewire 75 in order to facilitate the movement of the guidewire 75 through the channel 91. In some embodiments, the friction exerted on the guidewire 75 by the frictional member(s) 93 is only as much as is needed to move the guidewire 75, but not so much as to crush or deform the guidewire 75. The frictional member(s) 93 may be made out of any suitable material, such as but not limited to metal, rubber, elastomeric plastic or polymers, and the like.

In some embodiments, the frictional member(s) 93 may be a gear, wheel, or other rotating device. In at least one embodiment, a pair of frictional members 93 cooperatively engages the guidewire 75 for moving the guidewire 75 through the channel 91. For instance, as shown in FIGS. 16A and 16B, the frictional members 93 may be a pair of gears each having at least one, or preferably a plurality of teeth 94. The guidewire 75 is fed through the space between the frictional members 93, such that the teeth 94 of the frictional members 93 engage the guidewire 75. As the frictional members 93 rotate, the grip of the teeth 94 on the guidewire 75 pulls the guidewire 75 in the direction of the rotation.

In some embodiments, the teeth 94 of the frictional members 93 may interdigitate, such that when one frictional member 93 moves, the other moves as well, such as by rotation. One frictional member 93 may be actively rotated and the other frictional member 93 may be passive, free to spin or rotate as the active frictional member 93 moves it through the teeth 94 engagement. In other examples, both frictional members 93 of the pair may be actively moved or rotated, as described in greater detail hereinafter, in coordinated motions to move the guidewire 75. In still other embodiments, as illustrated in FIG. 16B, the teeth 94 of the paired frictional members 93 may not interdigitate, but rather come in close proximity to one another, grasping the guidewire 75 in between facing teeth 94. The pressure or friction of each of the teeth 94 on the guidewire 75 from opposite sides enables movement of the guidewire 75, as well as the rotation of one frictional member 93 to be transferred to the other. Therefore, only one frictional member 93 of a pair may be actively moved or rotated, with the other frictional member 93 being passive. However, it is contemplated that both frictional members 93 may be actuated in some embodiments.

In still other embodiments, there may be only a single frictional member 93, such as a slide bar or other like component (or simply the user's thumb) that may engage the guidewire 75 and, while applying slight pressure, may be slid or moved longitudinally along the axis 78 of the penetrating member 10 so as to move the guidewire 75 through the channel 91. Pressure may be removed from the slide bar to return it (possibly with aid of spring force) to its previous location within the housing, where it can be depressed again and moved again in order to continue advancing the guidewire 75 in a particular linear direction, such as by iterative distances.

In at least one embodiment, as shown in FIGS. 16A and 16B, the frictional member(s) 93 is actuated manually, such as by turning or rotating with a thumb or finger of a clinician using the device. In such embodiments, the housing 90 may include an aperture 95 through which at least a portion of the frictional member 93 is accessible for activation. For instance, a peripheral edge of a frictional member 93 may protrude slightly through the aperture 95, or may be flush with the aperture 95 such that a finger, thumb, or tool can be used to turn the frictional member 93. When multiple frictional members 93 are used, such with paired frictional members 93 as in FIG. 16B, one frictional member 93 may be actively turned or rotated, and the other frictional member 93 may be passive, rotating only as a result of actuation of the paired member. In such a case, the active frictional member 93 may be accessible through the aperture 95, while the other frictional member 93 may remain entirely within the housing 90. In other embodiments, both frictional members 93 may be actively turned.

In some embodiments, as in FIGS. 15A-15B, the device may include a guidewire actuator 96 that mechanizes the movement of the frictional member(s) 93. For instance, the guidewire actuator 96 may be a motor, such as an electromagnetic motor as is already known, which uses electrical energy to rotate or otherwise move a shaft 97. The shaft 97 may extend from the guidewire actuator 96 on one end to a frictional member(s) 93 on the other end. Rotation of the shaft 97 therefore rotates the attached frictional member 93. In this case, the frictional member 93 is an active frictional member 93. There may be a plurality of guidewire actuators 96 to employ a plurality of shafts 97, one for each corresponding frictional member 93. In at least one preferred embodiment, the guidewire actuator 96 includes a single shaft 97 that attaches to a single active frictional member 93. The active frictional member 93 may in turn cause a passive frictional member(s) 93 to also move or rotate. In still other embodiments, the shaft 97 may cause a hub, axel, or other mechanical device shared between frictional members 93, such that movement of the shaft 97 causes both or all frictional members 93 to move. In other embodiments, the guidewire actuator 96 may cause the frictional member(s) 93 to move linearly, rather than rotationally, such as in the case of slide bars or other type of frictional members 93.

It is contemplated that the guidewire actuator 96 is activated separately from the driving actuator 1 that generates reciprocating motion for the penetrating member 10. Hence, the penetrating member 10 may reciprocate independently of guidewire 75 movement. Of course, both the penetrating member 10 and guidewire 75 may be moved simultaneously. The guidewire actuator 96 and driving actuator 1 may be powered from the same power supply or different power supplies, which may be AC, DC, electromagnetic, battery, or other appropriate power supply.

In some embodiments, such as the "offset" configuration as seen in FIG. 15B, at least the penetrating member 10 and housing 90 are detachable from the handpiece body 1b that holds the driving actuator 1. The penetrating member 10 is inserted into the body of a patient, such as into a blood vessel beneath the skin. It must therefore be sterile with each new use. In addition, the guidewire 75 which is routed through the lumen 74 and housing 90 must also be sterile. Accordingly, any component that must be sterile should be detachable, and preferably disposable. The driving actuator 1, and guidewire actuator 96 in embodiments containing motorized guidewire actuation, may be retained and used repeatedly following re-sterilization process.

It should be understood from the above description that manual operation of the frictional member(s) 93 is possible in both the "offset" and "inline" configurations. Similarly, either the "offset" or "inline" embodiments may include a guidewire actuator 96 for mechanized actuation and movement of the guidewire 75, for example through penetrating member 10 and into a vessel.

In practice, the device is used to place a guidewire within the body, such as a within a blood vessel, vein, artery, organ, artificial tube, or other like structure. Specifically, the driving actuator 1 is actuated by a clinician or practitioner to produce reciprocating motion, which is transferred to the penetrating member 10. The vibrating distal end 12a of the penetrating member 10 pierces the skin of the patient, which is done with reduced force and less tissue deformation due to the oscillating vibrations. The penetrating member 10 is advanced to the target point within the blood vessel or tissue. During this insertion stage, the guidewire 75 remains outside the lumen 74 of the penetrating member 10, so that fluid flashback is permitted, such as to confirm proper entry into the desired location (e.g., blood from a vessel). Once the target area is reached by the distal end 12a, the driving actuator 1 may be deactivated to stop the reciprocating motion. In some embodiments, however, it may be desired to continue the reciprocating motion throughout the duration of use of the device. In still other embodiments, it may be desired to only activate the reciprocating motion during a portion of the insertion, for instance, only the vessel penetration phase while the device is not reciprocating at other times.

Figure 17:
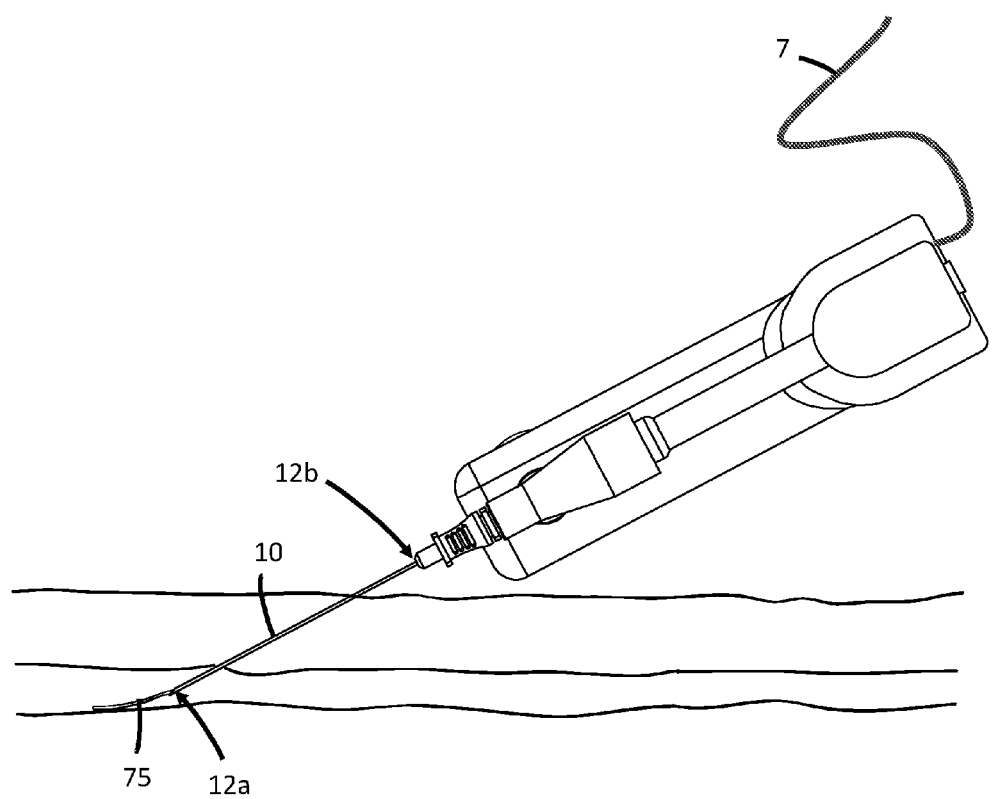
FIG. 17 is a schematic diagram of the device in use.

The guidewire actuator 96 may then be activated to advance the guidewire 75 into the lumen 74 of the penetrating member 10. In manual embodiments, the frictional member(s) 93 may be manually operated with the thumb or finger of the clinician or practitioner operating the device. Alternately, in some embodiments the clinician may use a finger or thumb as the frictional member 93 by directly contacting some portion of the guide wire and delivering axial force, for instance while pressing the guidewire between thumb and an opposing lower friction surface. As seen in FIG. 17, as the guidewire 75 advances, it passes through the open distal end 12a of the penetrating member 10 and into the target area. Feeding the guidewire 75 continues until the desired amount of guidewire 75 is placed as determined by the practitioner. Accurate guidewire 75 placement can therefore be performed with minimal disturbance of the penetrating member 10 by allowing continuous access to the interior of the lumen 74 without requiring the penetrating member 10 to first be detached from the device.

Now that exemplary embodiments of the present invention have been shown and described in detail, various modifications and improvements thereon will become apparent. While the foregoing embodiments may have dealt with the penetration through skin, bone, veins and ligaments as exemplary biological tissues, the present invention can undoubtedly ensure similar effects with other tissues which are commonly penetrated within the body. For example there are multiplicities of other tools like central venous catheter introducers, laparoscopic instruments with associated sharps, cavity drainage catheter kits, dialysis, and neonatal lancets, as well as procedures like insulin administration and percutaneous glucose testing, to name a few, where embodiments disclosed herein comprising sonically or ultrasonically driven sharps members may be used to precisely pierce or puncture tissues with minimal tinting/compression.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

REFERENCE LABELS

1 Driving Actuator
1b Handpiece body
2 Voice Coil
3 Centering Magnet
4 Magnet Assembly
4a Magnet Array
4b Opposite Magnet Array
4c Pole Piece
5 Motor Shaft
5b Motor Shaft Bearing
6 Keyed Coupler
7 Power Cable
8 VCM Body
8b VCM End Cap
9 Power Button
10 Penetrating Member
11 Hub
12 Bevel End
12a Distal end
12b Proximal end
13 Keyway
14 Keys
15 Coupling Piece with Side Port
16 Side Port
17 Compliant Tubing
18 Syringe Body
19 Plunger
20 Syringe Coupling Bracket
21 IV Catheter
22 Coupling Sled
22a Clips
22b Proximal End of Coupling Sled
23 Safety IV Device
24 Not Used
25 Penetrating member (IV Device)
26 Frequency Response of Driving Actuator in Air (non-loaded)
27 Frequency Response of Driving Actuator with Axial Force Applied (loaded)
28 Resonant Frequency in Air
29 Resonant Frequency with 1 N of Axial Force Applied
30 Oscillatory Displacement Damping at Original Resonant Frequency 31 Resonant Frequency Shift
32 Damping Resistant Operating Frequency
33 Simulated Frequency Response in Air
34 Simulated Frequency Response in Tissue
35 Resonant Displacement Peak in Air (simulated)
36 Displacement in Tissue at Original Resonant Frequency (simulated)
37 Resonant Displacement Peak in Tissue (simulated)
38 Operating frequency
39 Displacement at Operating Frequency in Air (simulated)
40 Displacement at Operating Frequency After Contacting Tissue (simulated)
41 Frequency Response Following Increase in Current (simulated)
42 Arrow
43 Displacement versus Insertion Depth Plot with Operating Frequency at 95 Hz
44 Displacement versus Insertion Depth Plot with Operating Frequency at 120 Hz
45 Displacement versus Insertion Depth Plot with Operating Frequency at 150 Hz
46 Attachment Clip
47 Syringe Adapter
48 Syringe View Window
49 Guide Shaft
49a Geared Guide Shaft
50 Guide Shaft Coupling
51 Syringe Coupler
52 Syringe Clip
53 Thumb Coupler
54 Drive Gear
54a Drive Gear Two
54b Idler Gear
55 Drive Gear Housing
56 Slider Device
57 Geared Slider Device
58 Section A-A
59 Section B-B
60 Section C-C
61 Section D-D
62 Foot Switch
63 Forward Position
64 Backward Position
65 Control Electronics Diagram
66 Axis of Rotation
67 Rotating Keyway Head
68 Rotating Motion
69 LVDT
70 LVDT Core
71 Resonant Frequency in Tissue (simulated)
74 Lumen
75 Guidewire
76 Directional arrow
77 Axis of driving actuator
78 Axis of penetrating member
80 Coupler
81 Oscillating coupler
82 Off-axis coupler
90 Housing
91 Channel
92 Guidewire port
93 Frictional member
94 Teeth
95 Housing aperture
96 Guidewire actuator
97 Shaft

What is claimed:

1. A device for guidewire placement, comprising:
an electrically activated driving actuator configured to generate repetitive reciprocating motion at a frequency in a range of 50 to 500 Hz in an axial direction sufficient to reduce the force needed to penetrate living being tissue when said driving actuator is activated;
a penetrating member having an open distal end and an opposite open proximal end, and further comprising a lumen extending between said open distal and proximal ends and dimensioned to accommodate a guidewire;
at least one coupler in mechanical communication connecting said driving actuator and said penetrating member and transmitting said repetitive reciprocating motion to said penetrating member to cause said penetrating member to move with said repetitive reciprocating motion at a frequency in a range of 50 to 500 Hz in said axial direction during penetration; and
at least one frictional member to selectively engage and facilitate movement of said guidewire through said lumen.

2. The device as recited in claim 1, further comprising a guidewire actuator that mechanizes movement of said at least one frictional member.

3. The device as recited in claim 2, wherein said guidewire actuator is a motor.

4. The device as recited in claim 1, wherein said at least one frictional member is moved manually.

5. The device as recited in claim 1, wherein said at least one frictional member rotates to move said guidewire in said lumen.

6. The device as recited in claim 1, further comprising a plurality of frictional members, wherein at least one of said frictional members is active.

7. The device as recited in claim 6, wherein at least one of said frictional members is passive and moves dependent on the movement of said at least one active frictional member.

8. The device as recited in claim 1, wherein said penetrating member is selectively attached to said coupler.

9. The device as recited in claim 8, wherein said penetrating member is disposable.

10. The device as recited in claim 1, further comprising a housing having a channel extending through at least a portion of said housing, said channel dimensioned to accommodate said guidewire and aligned with said lumen of said penetrating member.

11. The device as recited in claim 10, wherein said housing is connected to said penetrating member such that said lumen and said channel align in fluidic engagement and form a continuous bore.

12. The device as recited in claim 10, wherein said housing further comprises a housing aperture permitting access to said at least one frictional member.

13. The device as recited in claim 1, wherein said penetrating member extends axially along a penetrating axis, said driving actuator is configured to generate repetitive reciprocating motion along a driving axis, and wherein said penetrating axis is coaxial with said driving axis.

14. The device as recited in claim 13, further comprising a housing including said driving actuator, said at least one frictional member, and a channel dimensioned to accommodate said guidewire extending through at least a portion of said housing and through said driving actuator, such that said lumen of said penetrating member and said channel align in fluidic engagement and form a continuous bore.

15. The device as recited in claim 1, wherein said driving actuator comprises at least one of a voice coil, piezoelectric element, and a flextensional transducer.

16. A device for guidewire placement, comprising:
- an electrically activated driving actuator configured to generate repetitive reciprocating motion in an axial direction along a driving axis sufficient to reduce the force needed to penetrate living being tissue when said driving actuator is activated;
- a penetrating member having an open distal end and an opposite open proximal end and a lumen extending there between, said lumen dimensioned to accommodate a guidewire, said penetrating member and said lumen extending axially along a penetrating axis spaced apart from said driving axis;
- at least one coupler in mechanical communication between said driving actuator and said penetrating member, and transmitting said repetitive reciprocating motion from said driving axis to said penetrating member and moving said penetrating member with said repetitive reciprocating motion along said penetrating axis; and
- at least one frictional member configured to selectively engage and facilitate movement of said guidewire through said lumen.

17. The device as recited in claim 16, wherein said penetrating axis is parallel to said driving axis.

18. The device as recited in claim 16, wherein said coupler rigidly interconnects said penetrating member and said driving actuator to transfer said repetitive reciprocating motion from said driving axis to said penetrating axis.

19. The device as recited in claim 16, further comprising a guidewire actuator that mechanizes movement of said at least one frictional member.

20. The device as recited in claim 19, wherein said guidewire actuator is a motor.

21. The device as recited in claim 16, wherein said at least one frictional member is moved manually.

22. The device as recited in claim 16, wherein said at least one frictional member rotates to move said guidewire in said lumen.

23. The device as recited in claim 16, further comprising a plurality of frictional members, wherein at least one of said frictional members is active.

24. The device as recited in claim 23, wherein at least one of said frictional members is passive and moves dependent on the movement of said at least one active frictional member.

25. The device as recited in claim 16, wherein said penetrating member is selectively attached to said coupler.

26. The device as recited in claim 25 wherein said penetrating member is disposable.

27. The device as recited in claim 16, further comprising a housing having a channel extending through at least a portion of said housing, said channel dimensioned to accommodate said guidewire and aligned with said lumen of said penetrating member.

28. The device as recited in claim 27, wherein said housing is connected to said penetrating member such that said lumen and said channel align in fluidic engagement and form a continuous bore.

29. The device as recited in claim 27, wherein said housing further comprises a housing aperture permitting access to said at least one frictional member.

30. The device as recited in claim 27, wherein said penetrating member and said housing together are selectively attached to at least said coupler.

31. The device as recited in claim 30, wherein said penetrating member and said housing together are disposable.

32. The device as recited in claim 16, wherein said driving actuator comprises at least one of a voice coil, piezoelectric element, and a flextensional transducer.

* * * * *